US012790604B2

(12) United States Patent
Inui

(10) Patent No.: US 12,790,604 B2
(45) Date of Patent: Nov. 10, 2026

(54) CAPSULE PROTEIN AND MULTIMERIC COMPLEX COMPOSITION THEREOF, AND PHARMACEUTICAL COMPOSITION USING SAME

(71) Applicant: UNIVERSITY PUBLIC CORPORATION OSAKA, Osaka (JP)

(72) Inventor: Takashi Inui, Hyogo (JP)

(73) Assignee: UNIVERSITY PUBLIC CORPORATION OSAKA, Osaka (JP)

( * ) Notice: Subject to any disclaimer, the term of this patent is extended or adjusted under 35 U.S.C. 154(b) by 1241 days.

(21) Appl. No.: 17/612,613

(22) PCT Filed: May 19, 2020

(86) PCT No.: PCT/JP2020/019827
§ 371 (c)(1),
(2) Date: Apr. 19, 2022

(87) PCT Pub. No.: WO2020/235570
PCT Pub. Date: Nov. 26, 2020

(65) Prior Publication Data

US 2022/0275357 A1 Sep. 1, 2022

(30) Foreign Application Priority Data

May 20, 2019 (JP) ................................ 2019-094819

(51) Int. Cl.

| | |
|---|---|
| ***A61K 47/42*** | (2017.01) |
| ***A23L 33/17*** | (2016.01) |
| ***A61K 9/19*** | (2006.01) |
| ***A61K 9/50*** | (2006.01) |
| ***A61K 31/4745*** | (2006.01) |
| ***C12N 9/90*** | (2006.01) |

(52) U.S. Cl.
CPC ................ *C12N 9/90* (2013.01); *A23L 33/17* (2016.08); *A61K 9/19* (2013.01); *A61K 9/5052* (2013.01); *A61K 31/4745* (2013.01); *C12Y 503/99002* (2013.01); *A23V 2002/00* (2013.01)

(58) Field of Classification Search
None
See application file for complete search history.

(56) References Cited

U.S. PATENT DOCUMENTS

2005/0176070 A1 8/2005 Auton
2006/0199180 A1* 9/2006 Macina .................. C07K 14/47 435/6.14
2015/0031618 A1* 1/2015 Skerra ................ C07K 14/8114 435/69.6

FOREIGN PATENT DOCUMENTS

| | | |
|---|---|---|
| CN | 101426534 A | 5/2009 |
| JP | 2004-501180 | 1/2004 |
| JP | 2008-120793 | 5/2008 |
| JP | 2011-207830 | 10/2011 |
| JP | 2013-162760 | 8/2013 |
| WO | 02/00194 | 1/2002 |
| WO | WO 2013/118502 A1 | 8/2013 |

OTHER PUBLICATIONS

Howes, Laura, "Deepmind ai predicts protein structures." C&EN, issue of Dec. 1, 2020.*
Betts, Scott et al, "Buried hyudrophobic side chains essential for the folding of the parallel beta helix domains of the p22 tailspike." Prot. Sci. (2004) 13 p. 2291-2203.*
Guo, Haiwei H. et al, "Protein tolerance to random amino acid change." PNAS (2004) 101(25) p. 9205-9210.*
Yampolsky, Lev et al, "THe exchangeability of amino acids in proteins." Genetics (2006) 170 p. 1459-1472.*
Lowe, Derek, "Not alphafold's fault." blog "In the pipeline" entry of Sep. 7, 2022.*
Alteen, Mathew G. et al, "PHage display uncovers a sequence motif that drives polypeptide binding to a conserved regulatory exosite of 0-glcnac transferase." PNAS (2023) 120(42) e2303690120.*
Machine translation of WO2013118502.*
Shimoji, Masahiro et al., "Development of tumor-specific drug delivery system by multimerization of In vivo transport protein", The annual meeting of the Japanese biochemical society, Abstracts, 2017, vol. 90, p. 3P-1398, 4P1T27-04, along with an English translation thereof.
International Search Report issued in International Patent Application No. PCT/JP2020/019827, dated Jul. 21, 2020, along with an English translation thereof.
EESR for EP App. No. 20810360.6, dated Jun. 7, 2023.
Fukuhara et al., "Drug delivery system for poorly water-soluble compounds using lipocalin-type prostaglandin D synthase", Journal of Controlled Release, 159:143-150 (2012).
Nakatsuji et al., "Human Lipocalin-Type Prostaglandin D Synthase-Based Drug Delivery System for Poorly Water-Soluble Anti-Cancer Drug SN-38", PLOS ONE, 10(11):e0142206, doi:10.1371/journal.pone.0142206 (2015).
Office Action for CN App. No. 202080038078.6, dated Dec. 27, 2023 (w/ translation).

(Continued)

*Primary Examiner* — Fred H Reynolds
(74) *Attorney, Agent, or Firm* — Greenblum & Bernstein, P.L.C.

(57) ABSTRACT

There has been an idea to load a pharmaceutical agent in a barrel structure of a lipocalin-type prostaglandin D synthase, and to seal the pharmaceutical agent in the barrel structure by introducing a disulfide bond between H2-helix and E-F loop.
However, in some cases the pharmaceutical agent is released through a gap in the vicinity of the open mouth of the barrel structure.
The present capsule protein has substitution of alanine residue for a cysteine residue of the active center of the human lipocalin-type prostaglandin D synthetase. The protein further has substitution of barrier amino acid residue(s) for at least one amino acids of D strand. The barrier amino acids in the D-strand, located in the vicinity of the open mouth of its barrel structure suppresses the leak of the pharmaceutical agent.

9 Claims, 13 Drawing Sheets

Specification includes a Sequence Listing.

(56) References Cited

OTHER PUBLICATIONS

Fang et al., “Genetically Encoded Peptide-protein Reactive Pairs,” Acta Polymerica Sinica, 4:429-444, (2018) [Abstract; CN OA (cite C01)].
Liu et al., “Construction and Expression of the Recombinant Expressing Plasmids for the Tetrameric Leader Chain of Swine ß2m,” China Animal Husbandry and Veterinary Medicine, 40(4):77-81, (2013) [Abstract; CN OA (cite C01)].
Li et al., “The Improvement of Tetramer by the Peptide-HLA-A2 Fusion Protein,” J. Shanxi Aric. Univ., 5(6):11-15 (2007) [Abstract; CN OA (cite C01)].

* cited by examiner

CAPSULE PROTEIN AND MULTIMERIC COMPLEX COMPOSITION THEREOF, AND PHARMACEUTICAL COMPOSITION USING SAME

TECHNICAL FIELD

The present invention relates to a capsule protein and a multimeric composition thereof that can be used as a drug delivery system (DDS). Specifically, it is directed to a capsule protein that will allow poorly water-soluble drugs to have improved solubility and to release in affected areas after administration, a pharmaceutical composition, and a processed food thereof.

BACKGROUND ART

Development of drug carriers has been moving forward as a key technology in DDS. In the process of the development, the technology of interest includes e.g., liposomes, microparticles, nanomaterials, drug-polymer conjugates, and the like. Among them, polymer micelles have attracted attention as carriers advantageous for delivery of poorly water-soluble drugs. For examples, Patent Literature 1 discloses a micelle-forming composition including a hydrophobic core surrounded by a hydrophilic shell made of PVP (N-vinyl-2 pyrrolidone).

Patent Literature 2 discloses modified forms of a biological product, lipocalin-type prostaglandin D synthase (hereinafter referred to as "L-PGDS"). It reads that the modified products allow poorly water-soluble drugs to dissolve in water and to demonstrate pharmaceutical effects when administrated. The capsule protein, i.e., modified L-PGDS originates from in vivo products. Therefore, it is unlikely to be antigenic or toxic substance for humans, so that it can be said to serve as a safer and more reliable drug carrier.

Patent Literature 3 discloses a capsule protein including modified L-PGDS with targeting signals for recognizing cells in an affected area. An illustrative capsule protein is disclosed to include modified L-PGDS with a signal peptide that specifically binds to cancer cells to accumulate in cancer cells of an affected area, thereby producing improved therapeutic effects.

Patent Literature 4 discloses a capsule protein including modified L-PGDS that has substitution of two cysteine residues for tryptophan residues at positions 34 and 92 from its N-terminus, to form a disulfide bond between the cysteine residues. This gives the capsule protein a "lid" that can be opened and closed in response to an oxidation-reduction environment. The open-close functioning disulfide bond was intended to have improved drug holding capacity.

CITATION LIST

Patent Literature

Patent Literature 1: JP 2004-501180 W

Patent Literature 2: JP 2008-120793 A

Patent Literature 3: JP 2011-207830 A

Patent Literature 4: JP 2013-162760 A

SUMMARY OF INVENTION

Technical Problem

L-PGDS-based capsule protein enables a poorly water-soluble drug to dissolve easily. The protein has an advantage of high safety since it is derived from in vivo products. However, the protein possesses a barrel structure, i.e., a no lid container-shape which available containing drugs therein. One problem is that some drugs once taken in may leak out of the protein during transportation. Patent Literature 4 suggests one solution to such a problem, that is, forming a disulfide bond in the capsule protein to tighten the open mouth of the L-PGDS.

However, in some cases, the disulfide bond formed in the open mouth of the L-PGDS-based capsule protein was found to serve a limited function of blocking its open mouth.

Solution to Problem

The present inventor has conceived the disclosure herein in view of the above problems. It provides a capsule protein including amino acid residue(s) serving as a bulky barrier at the open mouth of its barrel structure. Such a protein would prevent unnecessary release of drugs therein.

More specifically, the present invention provides a capsule protein including human lipocalin-type prostaglandin D synthase, wherein the synthase has substitution of alanine (A) for cysteine (C) at active center thereof, and one or more substitution of barrier amino acid residue(s) for amino acid residue(s) of its β-strand "D".

Advantageous Effects of Invention

The capsule protein described herein would enable drugs to be delivered more efficiently to cells in an affected area since the capsule protein includes a mutant L-PGDS having its barrel structure made of β-strands; and the barrier amino acid residues in the open mouth of its barrel structure contribute to less leakage of the drugs from the capsule protein during transportation.

In addition, multimeric compositions of the capsule proteins would promote utilization of enhanced permeability and retention (EPR) effects, resulting in specific uptake by cancer cells and enhancing the effectiveness of the drug. At the same time, it is expected to suppress the effect on normal cells and reduce side effects.

DESCRIPTION OF EMBODIMENTS

Hereinafter, the present capsule protein will be described with reference to drawings and examples. Note that the following description exemplifies one embodiment and one example of the present invention, and the present invention is not limited to the following description. The following description can be modified without departing from the spirit of the present invention.

The present capsule protein is based on human lipocalin-type prostaglandin D synthase (L-PGDS). Table 1 shows an amino acid sequence of L-PGDS (SEQ ID NO: 1). This L-PGDS is composed of 168 amino acid residues from alanine at N-terminus to glutamine at position 168.

TABLE 1

SEQ ID NO: 1 [Original L-PGDS (before deactivation)]

| | | | | |
|---|---|---|---|---|
| 10 | 20 | 30 | 40 | 50 |
| APEAQVSVQP | NFQQDKFLGR | WFSAGLASNS | SWLREKKAAL | SMCKSVVAPA |
| 60 | 70 | 80 | 90 | 100 |
| TDGGLNLTST | FLRKNQCETR | TMLLQPAGSL | GSYSYRSPHW | GSTYSVSVVE |
| 110 | 120 | 130 | 140 | 150 |
| TDYDQYALLY | SQGSKGPGED | FRMATLYSRT | QTPRAELKEK | FTAFCKAQGF |
| 160 | 168 | | | |
| TEDTIVFLPQ | TDKCMTEQ | | | |

The term “mutant L-PGDS” or “mutant” herein refers to a L-PGDS variant, obtained through transformation of *E. coli*. Table 2 shows an amino acid sequence of a mutant L-PGDS (SEQ ID NO: 2). For convenience of artificial synthesis, two amino acid residues, Glycine-Serine (GS), were added to N-terminus of the sequence, as shown in Table 1. Unless otherwise stated herein, the amino acid sequence of “mutant L-PGDS” represents the sequence including GS added to N-terminus of that of L-PGDS.

TABLE 2

SEQ ID NO: 2 C45A/C147A sequence

| | | | | |
|---|---|---|---|---|
| 10 | 20 | 30 | 40 | 50 |
| GSAPEAQVSV | QPNFQQDKFL | GRWFSAGLAS | NSSWLRE**K**KA | ALSMAKSVVA |
| 60 | 70 | 80 | 90 | 100 |
| PATDGGLNLT | STFLRKNQCE | TRTMLLQPAG | SLGSYSYRSP | **H**WGSTYSVSV |
| 110 | 120 | 130 | 140 | 150 |
| VETDYDQYAL | LYSQGSKGPG | EDFRMATLYS | RTQTPRAELK | EKFTAFAKAQ |
| 160 | 170 | | | |
| GFTEDTIVFL | PQTDKCMTEQ | | | |

For loss of enzymatic activity, the mutant L-PGDS was designed to have substitution of alanine (A) residue for its active site cysteine (C) residue at position 45 from the N-terminus, corresponding to C43 in SEQ ID NO: 1. Further, the mutant was also designed to have substitution of “A” residue for “C” residue at position 147, corresponding to C145 in SEQ ID NO: 1. This was intended to introduce no undesired disulfide bonds into the mutant. Those two positions were indicated by boxed characters. This mutant L-PGDS is also called “C45A/C147A”.

Figure 1:
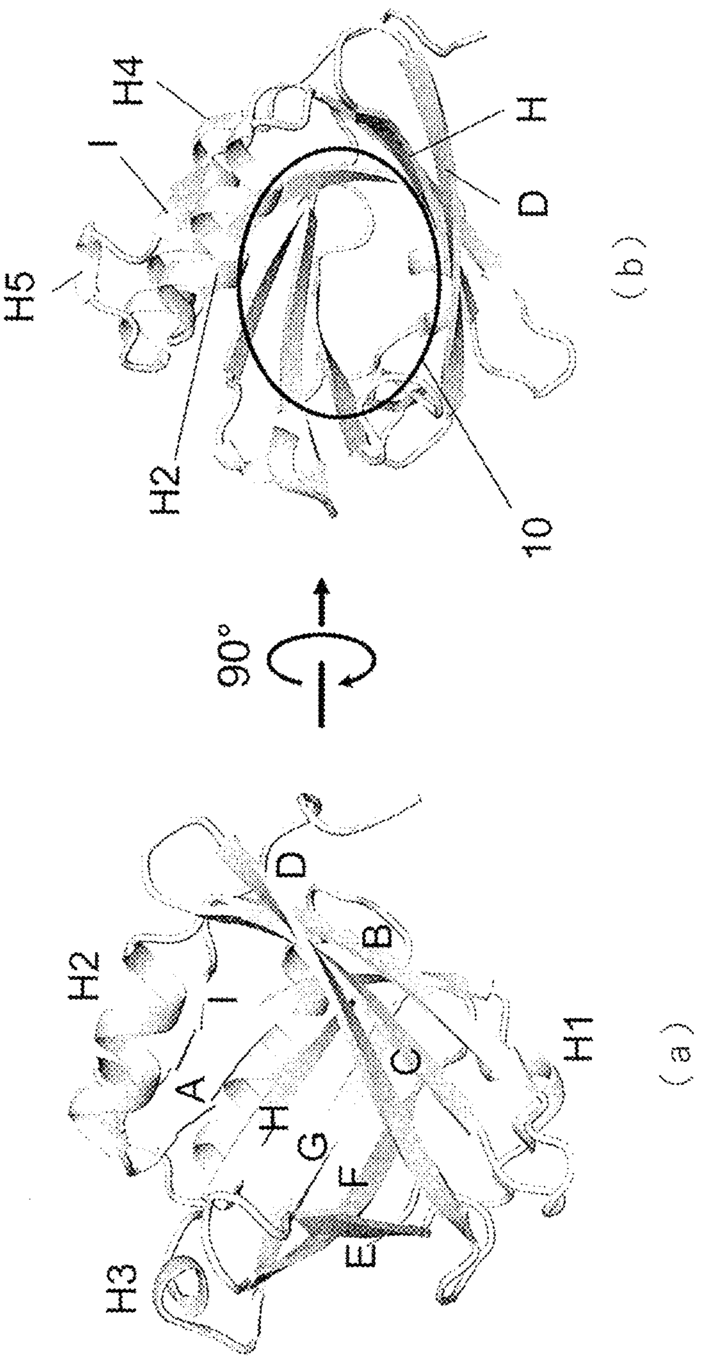
FIG. 1 is a diagram illustrating crystal structure models of a mutant L-PGDS.
Figure 2:
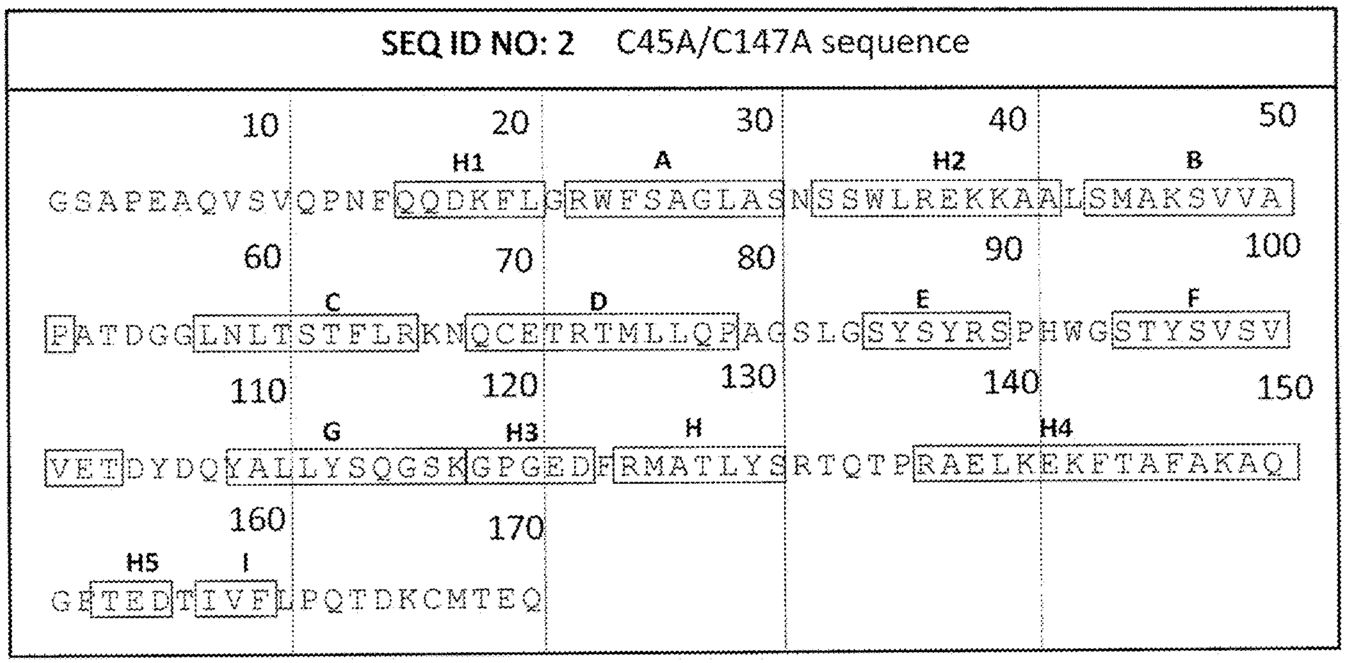
FIG. 2 is a diagram showing an amino acid sequence of a mutant L-PGDS.

FIG. 1 shows a crystal structural model of the mutant L-PGDS. FIG. 1 (*a*) and (*b*) show a view and other view after 90-degree rotation of the model, respectively. L-PGDS also has the same overall conformation as that of the mutant. In addition, FIG. 2 shows β-strands and α-helices corresponding to the amino acid sequence (SEQ ID NO: 2) of the mutant L-PGDS (C45A/C147A).

The mutant L-PGDS has eight β-strands and three α-helices. The individual β-strands are labeled A to H; and the α-helices are labeled H1 to H3. The mutant further includes loops between the β-strands; and short strand “I” and short helices H4 and H5.

The β-strands A to H twist and coil to form a closed toroidal structure, i.e., a barrel structure. The barrel structure is considered to enable the mutant L-PGDS to hold a pharmaceutical agent in its center cavity. As shown in FIG. 1(*b*), the region between D-strand and H2-helix forms a large open mouth 10 of the barrel structure.

The open mouth 10 may release a pharmaceutical agent hold in the cavity before the agent reaches e.g., desired cells. In light of the above, Patent Literature 4 discloses a “lid” for the open mouth 10. The publication discloses that the disulfide bond forms between EF-loop and H2-helix, and the E-F-loop represents the loop that connects E-strand and F-strand of the mutant.

Referring again to FIG. 2, E-F loop is composed of 4 amino acid residues from proline (P) at position 90 to glycine (G) at position 93 from the N-terminus of the mutant L-PGDS. Similarly, H2-helix is composed of 10 amino acid residues from serine (S) at position 32 to alanine (A) at position 41 from the N-terminus. A disulfide bond can be obtained by changing one residue in each region of EF-loop and H2-helix to cysteine (C). This is called “disulfide clip” or “D-clip”.

Figure 3:
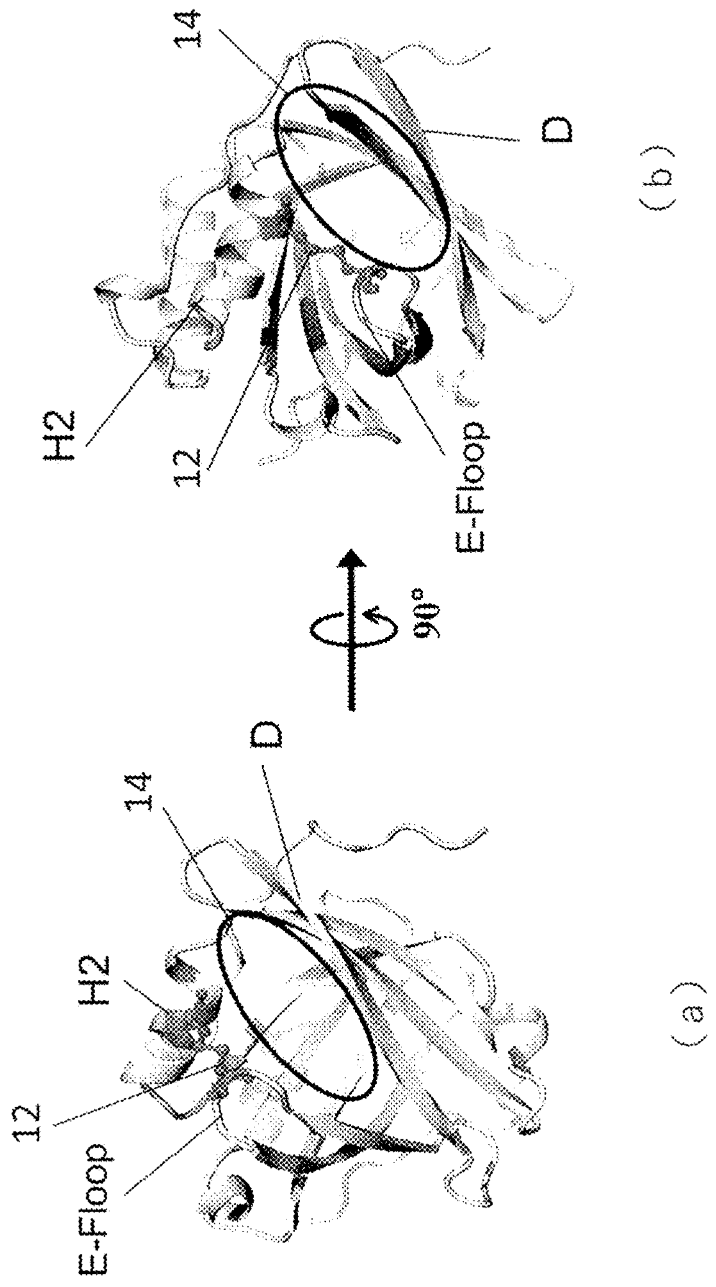
FIG. 3 is a diagram illustrating structure models of a "D-clip" mutant into which D-clip (disulfide bond) is introduced.

For example, FIG. 3 shows a structure model of the mutant L-PGDS. The mutant has substitution of two cysteines (C) for lysine (K) in H2-helix at position 38 from the N-terminus and histidine (H) in E-F loop. The two cysteines form a disulfide clip 12 to lid a part of the open mouth 10. The mutant L-PGDS is called “D-clip mutant”. Patent Literature 4 discloses a D-clip mutant.

However, the disulfide clip 12 was found to merely clip an end of the open mouth 10, resulting in leaks of the drug loaded in the barrel structure from a gap 14 between the disulfide clip 12 and D-strand. Therefore, in order to seal the gap 14 on D-strand, a barrier amino acid is provided in an embodiment of the present invention. The barrier amino acid refers to an amino acid capable of reducing aperture area of the open mouth 10. By providing the barrier amino acid, it is possible not only to seal the gap 14 but also to effectively reduce the aperture area of the open mouth 10.

Referring again to FIG. 2, D-strand spans 11 amino acid residues from glutamine (Q) at position 68 to proline (P) at position 78 from the N-terminus of the mutant L-PGDS. Barrier amino acid residues should have a bulky functional group so as to seal the gap 14 as much as possible. Further, the introduction of a barrier amino acid residue into D-strand of the mutant L-PGDS should not significantly destroy the overall structure of the mutant so as to maintain its barrel structure.

The barrier amino acid includes but not limited to, e.g., lysine (K), histidine (H), tryptophan (W), tyrosine (Y), phenylalanine (F) and the like. In addition, substitution may occur one or more sites. Moreover, the barrier amino acid may be inserted into the sequence of amino acid residues spanning the β-strand.

Figure 4:
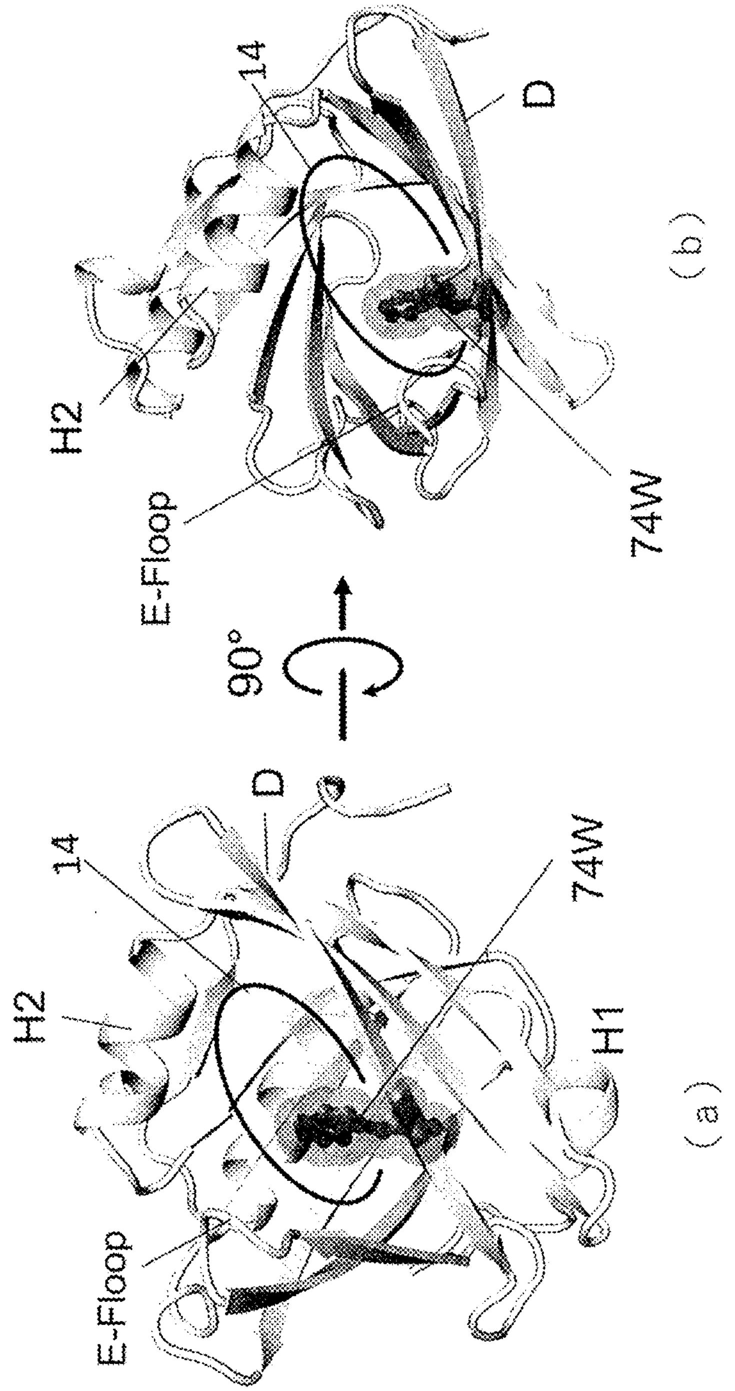
FIG. 4 is a diagram illustrating structure models of a barrier-attached mutant to which a "barrier-attached amino acid" is added.

FIG. 4 shows structure models of the mutant L-PGDS having substitution of tryptophan (W) for methionine (M) in D-strand at position 74 from the N-terminus (See also FIG. 2). The figure indicates the tryptophan residue as "74W". The figure illustrates that the tryptophan arranged in D-strand would close the gap 14. The mutant L-PGDS provided with the barrier amino acid as described above is called a "barrier-attached mutant".

A disulfide clip can also be provided in the barrier-attached mutant. A mutant L-PGDS provided with both of the barrier amino acid and a disulfide clip is called a "barrier-attached D-clip mutant".

Furthermore, as shown in Patent Literature 3, a targeting peptide or a peptide that recognizes a target cell can be also added to N-terminus, C-terminus, or both of the mutant. Such targeting peptides can be not only bound to the terminus (s) of the mutant, but also included in the mutant as partially overlapping sequence. The targeting peptides include but not limited to, e.g., NGR that specifically binds to a membrane protein (CD13) expressed in a neovascular endothelial. Moreover, it may be an internalized-Arg-Gly-Asp (iRGD) motif that recognizes αvβ3 and αvβ5 integrins, or a Cys-Arg-Gly-Asp-Lys (CRGDK) motif that recognizes Neuropilin-1.

Further, the exemplary motifs suitable for the present invention are as follows: Lys-Leu-Pro (KLP) motif (Cancer Res, 97, 1075-81, 2006), which recognizes a peritoneal tumor of gastric cancer; Asn-Val-Val-Arg-Gln (NVVRQ) motif (Clin Cancer Res, 14, 5494-502, 2008), which recognizes a metastatic cancer cell; Phe-Gln-His-Pro-Ser-Phe-Ile (FQHPSFI) motif (Mol Med, 13, 246-54, 2007), which recognizes a liver cancer cell, and the like.

The term "targeting barrier-attached mutant" refers to a capsule protein as an embodiment of the present invention, specifically a barrier-attached mutant having a targeting peptide. The term "targeting barrier-attached D-clip mutant" refers to a targeting barrier-attached mutant that further includes the disulfide clip(s). In addition, for convenience of genetic recombination, a plurality of amino acid residues may be added to N-terminus or C-terminus of the capsule protein according to the present invention. Such amino acid residues include but not limited to e.g., Glycine-Serine (GS).

In an embodiment of the present invention, the capsule protein can incorporate a compound having a size of up to about 800 Da into the barrel structure. The compound may be a pharmaceutical agent or other compounds. Such other compounds may include e.g., an auxiliary nutrient or a naturally occurring compound.

In addition, enhanced permeability and retention (EPR) effect is known to contribute to increase in tumor cell specific uptake of a drug in DDS, and enhanced drug retention, resulting in prolonged drug action. Therefore, the barrier-attached mutants, or an embodiment of the present capsule protein would form a multimeric composition. The entire size of the composition is designed to be 10 nm or more for taking advantage of the EPR effect. Moreover, a targeting peptide may be added to the multimeric composition.

Figure 5:
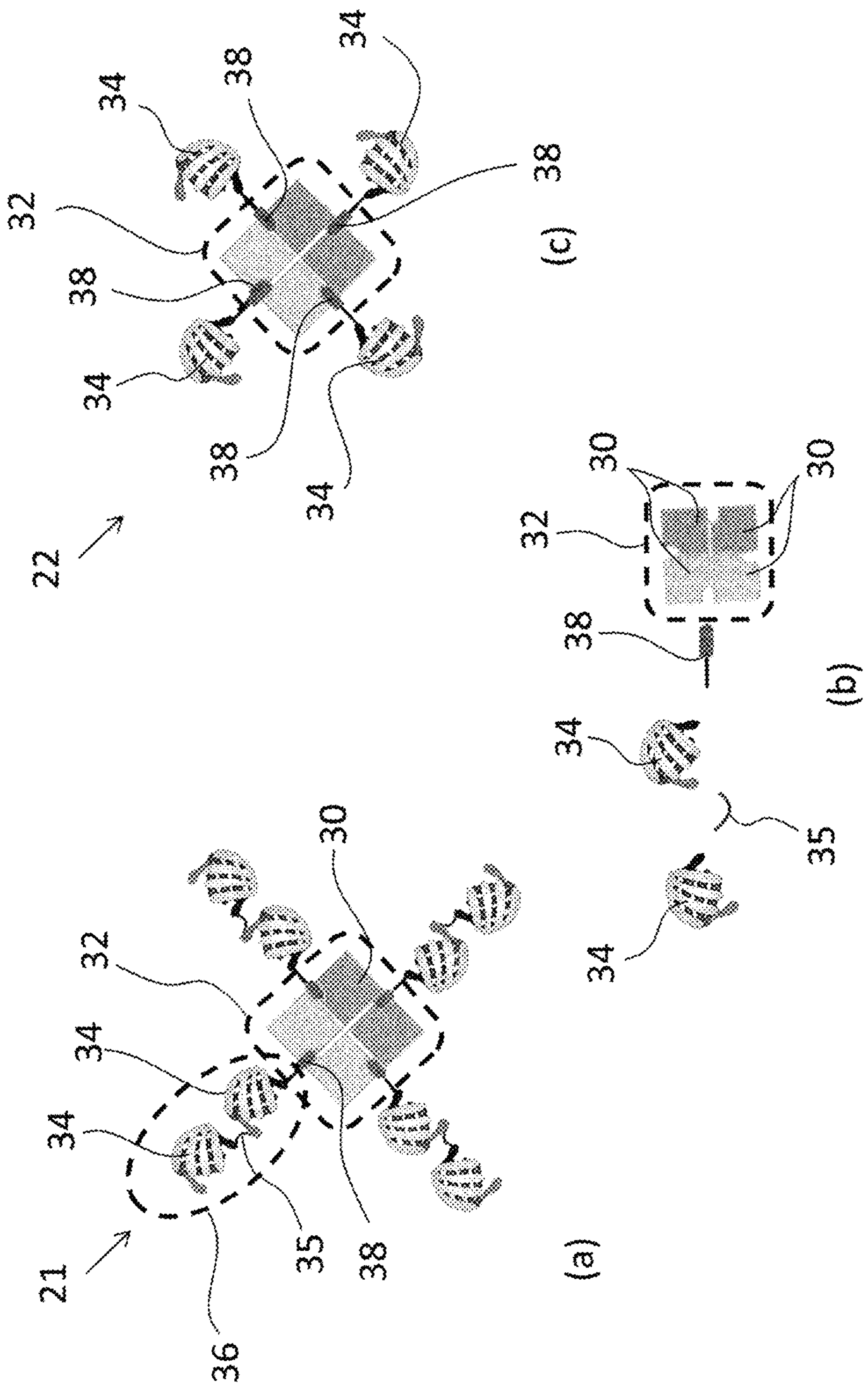
FIG. 5 is a diagram illustrating concepts of a multimeric composition.

The capsule proteins can be linearly linked through bonds between their C-termini and N-termini, thereby forming multimeric compositions. However, in a preferable embodiment, the capsule proteins are arranged in a radial fashion and linked to one another. FIG. 5 shows conceptual diagrams of structures of a multimeric composition of the capsule proteins, as used in an embodiment of the present invention.

FIG. 5(*a*) shows a conceptual diagram of the multimeric composition of the capsule proteins (hereinafter, it is simply called a "multimeric composition"). FIG. 5(*b*) is a partially exploded view of a multimeric composition 21. The multimeric composition 21 includes four dimers 36, each of which has two capsule proteins 34. The two capsule proteins 34 are bound via a linker 35 to each other. The dimers 36 are linked via biotins 38 to a tetrameric streptavidin 32 consisting of its monomers 30. The resultant multimeric composition 21 forms as an octameric composition of the capsule proteins 34.

As the capsule protein 34, mutant L-PGDS or a barrier-attached mutant can be suitably used. Embodiments of barrier-attached mutants will be described in the following sections.

The dissociation constant ($K_d$) of the biotin 38-streptavidin 30 complex is determined to be $10^{-15}$M. Their binding is classified as one of the strongest non-covalent interactions between known proteins and their ligands. Further, their binding is formed very quickly; and their binding, once formed, is hardly affected by pH, temperature, modifiers, organic solvents, and the like. Moreover, biotinylating molecules is unlikely to disturb the natural function of the molecule since biotin per se is a small molecule. Therefore, the octamer in FIG. 5(*a*) is thought to be extremely stable.

FIG. 5(*c*) shows a multimeric composition 22 that includes monomers of the capsule proteins 34, each of which is bound via the biotin 38 to the tetrameric streptavidin 32 consisting of its monomers 30. This forms a tetramer of the capsule proteins 34.

As will be described later, the multimeric composition 21 including eight capsule proteins 34, or the octameric composition has a diameter of 10 nm or more. That is, the octameric composition is larger than the tetramer or the monomer of the protein(s). Therefore, the multimeric composition 21 tends to enter defective endothelial cells of tumor blood vessels through their wider fenestrations than those of normal cells while the composition tend not to enter normal cells. Therefore, the octameric multimeric composition 21 exhibits a so-called EPR effect, resulting in tumor specific uptake and accumulation in tumor of the composition.

As will be described later, the multimeric composition 21 has demonstrated an effect clearly different from that of the monomer of the capsule protein. The ESR effect is thought to be one of factors causing this difference. In this regard, we will describe in the later sections, in vivo experiments with octamers of the capsule proteins 34.

The capsule proteins become soluble after taking in a pharmaceutical agent or other compounds. This property of the capsule proteins would be maintained even if they form a multimeric composition. Therefore, the capsule proteins can be suitable for solubilizing poorly soluble drugs, poorly soluble vitamins, and the like. The capsule proteins may apply to solubilization of SN-38, vitamins A, D, E, and K, thyroid hormones, steroid hormones, isoflavones, and the like. Furthermore, the capsule proteins will solubilize poorly soluble substances. This means that it overcomes a difficult challenge, i.e. "solubilization" in drug development.

A pharmaceutical agent contained or encapsulated in the present capsule proteins can be provided as pharmaceutical composition (hereinafter, simply called a "pharmaceutical composition".) The pharmaceutical composition can be provided in liquids and solutions. Further, it can also be provided as powder made by e.g., freeze-drying. As described in Patent Literature 3, the effect is maintained even when freeze-dried.

Thus, routes of administration of the pharmaceutical composition can be oral or parenteral. That is, the pharmaceutical composition is administered orally or parenterally (e.g., intravenously, subcutaneously, or intramuscular injection, topically, rectally, transdermally, or nasally). Illustrative examples of the composition for oral administration include tablets, capsules, pills, granules, powders, solutions, suspensions, and the like.

Also, illustrative examples of the composition for parenteral administration include aqueous agents or oily agents for injection, ointments, creams, lotions, aerosols, suppositories, patches, and the like. These formulations are prepared using conventionally known techniques, and can contain non-toxic and inert carriers or excipients commonly used in the field of pharmaceutical formulation.

In addition, the complexes that incorporate drugs or non-drug compounds into the capsule proteins can also be provided as processed foods. Examples of the processed foods include not only general processed foods but also foods with health claims such as foods for specified health uses and foods with nutrient function claims prescribed in the food with health claims system of the Ministry of Health, Labour, and Welfare, and nutritional supplementary foods (supplements), feeds, food additives, and the like are also included in the processed foods. The general processed foods include favorite foods and health foods such as candies, gums, jellies, biscuits, cookies, rice crackers, breads, noodles, fish meat/meat paste products, tea, soft drinks, coffee beverages, milk beverages, whey beverages, lactic acid bacteria beverages, yogurts, ice creams, and puddings. Further, it may be used as an industrial product or an industrial material by utilizing a property of solubilizing a poorly soluble substance.

In embodiments of the present invention, the processed foods can be prepared by adding a capsule protein (complex) containing other compound to the raw materials of these processed foods. The capsule proteins, or a barrier-attached mutants would function as a carrier encapsulating another compound, but they per se are proteins. Therefore, it is preferable to avoid heat-induced denaturation of the proteins during the production process; specifically, to avoid the heating process as much as possible at or after the point of addition of the proteins to intermediates.

EXAMPLES

The inventor has prepared four types of capsule proteins for samples as follows:

(1) mutant L-PGDS;
(2) targeting mutant L-PGDS;
(3) barrier-attached D-clip mutant; and
(4) targeting barrier-attached D-clip mutant.

The mutant L-PGDS was the capsule protein shown in SEQ ID NO: 2. The mutant, as previously referred to as "C45A/C147A", was designed to have substitution of alanine (A) residues at its positions 45 and 147 from N-terminus, for two cysteine (C) residues of its wild type's. That is, the alanine residue in the mutant instead of cysteine (C) residue in the corresponding L-PGDS's active site was intended for loss of its enzymatic activity; and the alanine residue introduced at position 147 was intended to form no undesired disulfide bond in process of preparation.

Figure 6:
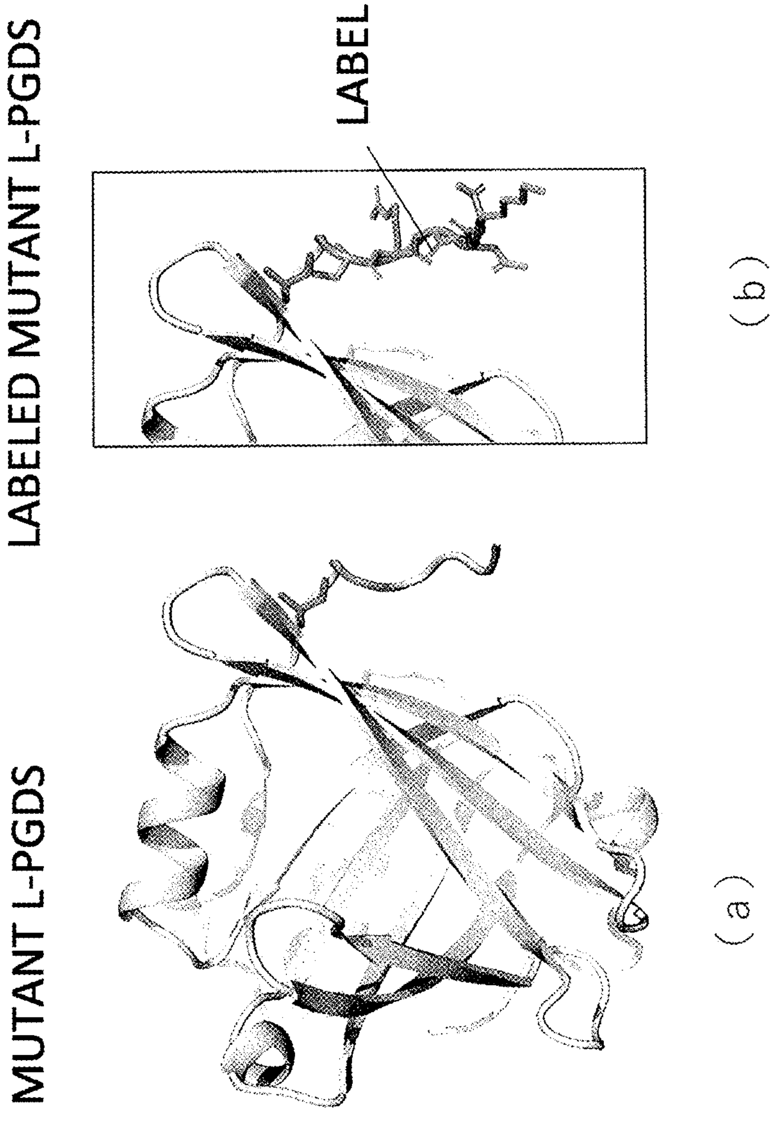
FIG. 6 is a diagram illustrating structure models of a mutant L-PGDS and a targeting mutant L-PGDS.

The targeting mutant L-PGDS was the mutant L-PGDS further including in its C-terminus, iRGD peptide (CRGDKGPDC: SEQ ID NO: 3) for simultaneously enabling accumulation in tumors and cell membrane permeation. The targeting peptide was included to partially overlap in primary structure with the mutant L-PGDS in its C-terminal sequence. This was intended to eliminate antigenicity to mice used in vivo experiments. The amino acid sequence of the targeting mutant L-PGDS is shown in Table 4 as SEQ ID NO: 4. The targeting peptide is indicated by solid square or "■". FIG. 6 shows structure models of the mutant L-PGDS and the targeting mutant L-PGDS molecules.

TABLE 3

| SEQ ID NO: 3 iRGD Peptide |
|---|
| 5 10 20 30 40 50 |
| CRGDKGPDC |

TABLE 4

| SEQ ID NO: 4 (Labeled mutant L-PGDS) | | | | |
|---|---|---|---|---|
| 10 | 20 | 30 | 40 | 50 |
| GSAPEAQVSV | QPNFQQDKFL | GRWFSAGLAS | NSSWLREKKA | ALSMAKSVVA |
| 60 | 70 | 80 | 90 | 100 |
| PATDGGLNLT | STFLRKNQCE | TRTMLLQPAG | SLGSYSYRSP | HWGSTYSVSV |
| 110 | 120 | 130 | 140 | 150 |
| VETDYDQYAL | LYSQGSKGPG | EDFRMATLYS | RTQTPRAELK | EKFTAFAKAQ |
| 160 | 170 | ■ | | |
| GFTEDTIVFL | PQTDK**CRGDK** | **GPDC** | | |

To produce the barrier-attached D-clip mutant, a barrier amino acid residue, specifically tryptophan (W) was first introduced to the protein instead of methionine (M) residue in the protein's D-strand. Specifically, the methionine was located at position 74 from the N-terminus of the mutant L-PGDS.

Further, the barrier-attached D-clip mutant was designed to have "D-clip". In this regard, the D-clip was formed by substitution of cysteines (C) for lysine (K) and histidine (H) residues located at positions 38 and 91, respectively from the N-terminus of the mutant L-PGDS. Table 5 shows the amino acid sequence of the barrier-attached D-clip mutant (SEQ ID NO: 5). In Table 5, the barrier amino acid is indicated by solid triangle or "▲". The D-clip (disulfide bond) is indicated by solid star or "★". The two cysteines, indicated by solid star or "★", would form a disulfide bond. Reducing environment drives separation of the disulfide bond, thereby allowing the D-clip to regulate switching between closed and opened states of the open mouth 10.

TABLE 5

| SEQ ID NO: 5 Barrier-attached D-clip mutant | | | | |
|---|---|---|---|---|
| 10 | 20 | 30 | ★40 | 50 |
| GSAPEAQVSV | QPNFQQDKFL | GRWFSAGLAS | NSSWLRECKA | ALSMAKSVVA |
| 60 | 70 | ▲ 80 | 90★ | 100 |
| PATDGGLNLT | STFLRKNQCE | TRTWLLQPAG | SLGSYSYRSP | CWGSTYSVSV |
| 110 | 120 | 130 | 140 | 150 |
| VETDYDQYAL | LYSQGSKGPG | EDFRMATLYS | RTQTPRAELK | EKFTAFAKAQ |
| 160 | 170 | | | |
| GFTEDTIVFL | PQTDKCMTEQ | | | |

Figure 7:
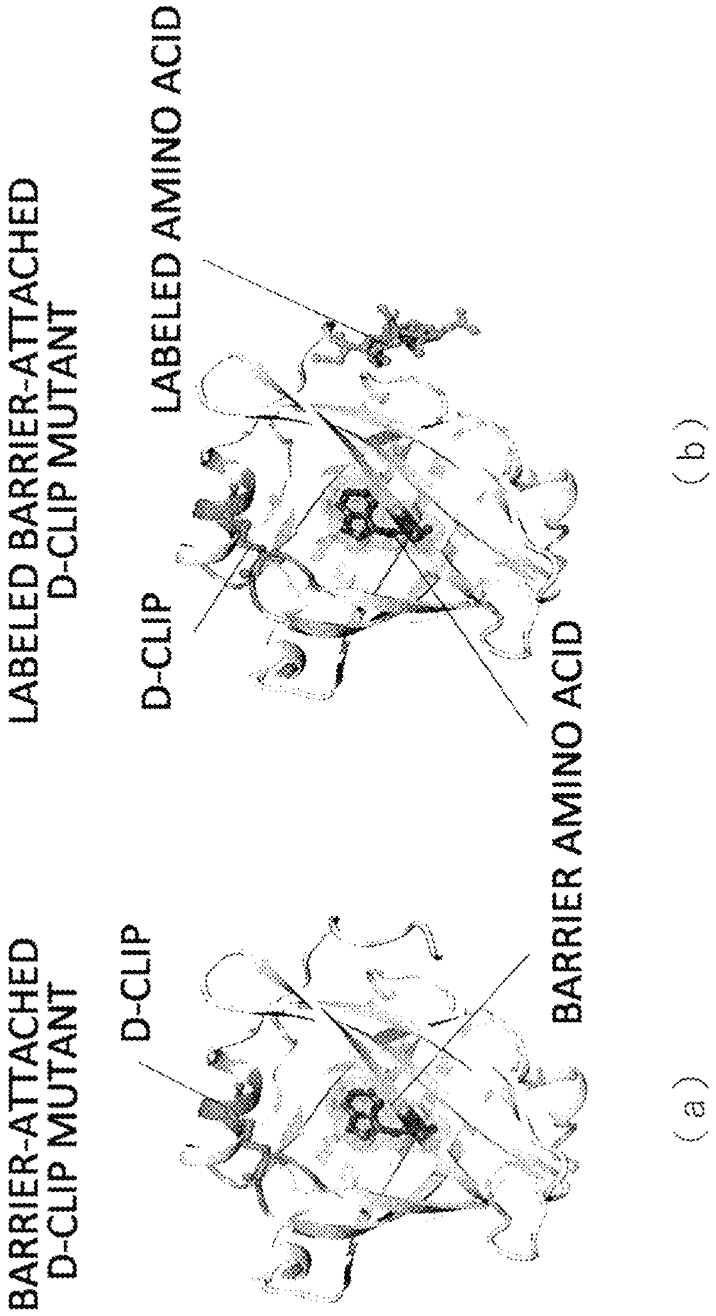
FIG. 7 is a diagram illustrating structure models of a barrier-attached D-clip mutant and a targeting barrier-attached D-clip mutant.

The targeting barrier-attached D-clip mutant was the barrier-attached D-clip mutant further including in its C-terminus, iRGD peptide (CRGDKGPDC). The targeting peptide was included to partially overlap in primary structure with the barrier-attached D-clip mutant (SEQ ID NO: 5). Table 6 shows the amino acid sequence of the targeting barrier-attached D-clip mutant (SEQ ID NO: 6). The barrier amino acid is indicated by solid triangle or "▲", and the D-clip (disulfide bond) is indicated by solid star or "★". Also, a portion of the targeting peptide is indicated by solid square or "■". In addition, FIG. 7 shows the structure model of a barrier-attached D-clip mutant and a targeting barrier-attached D-clip mutant.

TABLE 6

| SEQ ID NO: 6 Labeled barrier-attached D-clip mutant | | | | |
|---|---|---|---|---|
| 10 | 20 | 30 | ★40 | 50 |
| GSAPEAQVSV | QPNFQQDKFL | GRWFSAGLAS | NSSWLRECKA | ALSMAKSVVA |
| 60 | 70 | ▲ 80 | 90★ | 100 |
| PATDGGLNLT | STFLRKNQCE | TRTWLLQPAG | SLGSYSYRSP | CWGSTYSVSV |
| 110 | 120 | 130 | 140 | 150 |
| VETDYDQYAL | LYSQGSKGPG | EDFRMATLYS | RTQTPRAELK | EKFTAFAKAQ |
| 160 | 170 | ■ | | |
| GFTEDTIVFL | PQTDK**CRGDK** | **GPDC** | | |

The nucleotides coding for capsule proteins in Examples were ligated into expression vector plasmids. The "megaprimer" method was employed for preparation of the plasmids. The capsule proteins were expressed as a glutathione S-transferase fusion proteins in *E. coli* BL21 (DE3) strain.

The protein-expressing strains were cultured with shaking in LB/Amp test tube medium at 37° C. for 8 hours, then transferred to a 2×YT/Amp auto induction medium, and cultured with shaking at 37° C. for 16 hours. The resulting bacterial cells were ultrasonically disrupted, and the supernatants of the disrupted solutions were subjected to affinity chromatography with Glutathione-Sepharose 4B columns.

The fusion proteins adsorbed to the columns were incubated overnight with 165 units of thrombin to release target proteins; and the target proteins were then eluted and purified.

7-Ethyl-10-hydroxycamptothecin (abbreviated name "SN-38") was then encapsulated in the respective capsule proteins. SN-38 is a poorly water-soluble anticancer drug, and is known to show a high antitumor effect at a lower dose compared with irinotecan hydrochloride, a prodrug of SN-38 currently clinically used.

Drug Releasing Capacity

With a dialysis membrane (Dialysis Membrane, Size 27 Wako molecular weight cut-off: 14,000), each 5 mL of samples was each dialyzed against 150 mL of PBS as an external solution in an incubator at 37° C. for 72 hours. Each of the samples included the solution of SN-38/mutant L-PGDS, SN-38/barrier-attached D-clip mutant or SN-38/targeting barrier-attached D-clip mutant. The samples were prepared to contain 50 uM of SN-38 and 50 uM of the respective capsule proteins.

At 0, 1, 3, 6, 8, 12, 24, 36, 48, 60, and 72 hours after the start of dialysis, 500 μL of the external solution was sampled, and the same amount of PBS was added instead. SN-38 concentration in the sampled external solutions was measured with a fluorescence spectrophotometer F-7000 (HITACHI; excitation wavelength: 365 nm; measuring wavelength: 380 to 600 nm; and monitoring temperature: 37° C.).

Subsequently, drug release function in response to a reducing environment of the barrier-attached D-clip mutant and the targeting barrier-attached D-clip mutant was evaluated by equilibrium dialysis method in the same manner as described above. PBS and 10 mM DTT/PBS solutions were used as the external solutions for dialysis. The external PBS and 10 mM DTT/PBS solutions simulated oxidizing and reducing environments, respectively.

Figure 8:
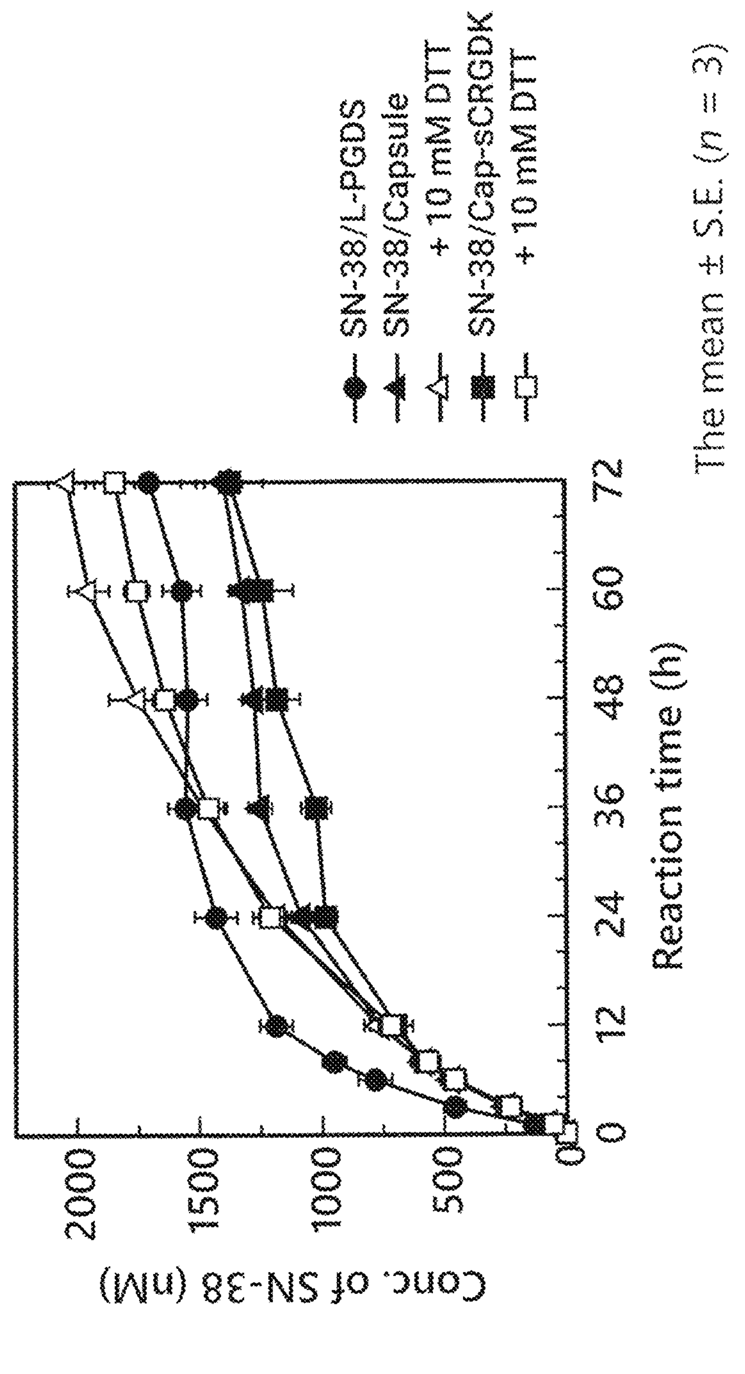
FIG. 8 is a graph examining holding force and releasing capacity when SN-38 is contained in a capsule protein.

FIG. 8 shows the time-dependent changes of SN-38 concentration in the external dialysis solution. The horizontal axis represents reaction time (hr), and the vertical axis represents SN-38 concentration (nM). Error bars represent the standard error of the mean, or mean±standard error (n=3). The abbreviations or symbols in the figure have the following meanings: "SN-38/L-PGDS" or "●" represents SN-38/mutant L-PGDS; "SN-38/Capsule" or "▲" represents SN-38/barrier-attached D-clip mutant; and "SN-38/Cap-sCRGDK" or "■" represents SN-38/targeting barrier-attached D-clip mutant. The symbols "Δ" and "□" with"+10 mM DTT" represent the results of the pharmaceutical compositions, i.e."SN-38/Capsule" and "SN-38/Cap-sCRGDK" in the presence of 10 mM DTT, respectively. The addition of DTT (Dithiothreitol) allows the solutions to have a strong reducing environment.

FIG. 8 shows that the barrier-attached D-clip mutant ("SN-38/Capsule") and the targeting barrier-attached D-clip mutant ("SN-38/Cap-sCRGDK") had maintained SN-38 lower concentrations in their external PBS solutions, than the mutant L-PGDS (SN-38/L-PGDS) had during the dialysis. The studies found that the release of SN-38 from the SN-38/barrier-attached D-clip mutant or the SN-38/targeting barrier-attached D-clip mutant had been suppressed as compared with the release from the SN-38/mutant L-PGDS.

The figure also indicates that the barrier-attached D-clip mutant ("SN-38/Capsule" or "Δ") and the targeting barrier-attached D-clip mutant ("SN-38/Cap-sCRGDK" or "□") had increased the SN-38 concentrations in the DTT/PBS external solutions as compared with the corresponding concentrations in PBS solutions.

From the above, the barrier-attached D-clip and the targeting barrier-attached D-clip mutants were shown to hold SN-38 molecules for a longer time than the L-PGDS mutant in the oxidizing environment, and to release the SN-38 molecules in response to the reducing environment. Further, the barrier-attached D-clip and the targeting barrier-attached D-clip mutants had no difference in drug release behavior, indicating that the addition of the targeting peptide does not affect drug release control.

Figure 9:
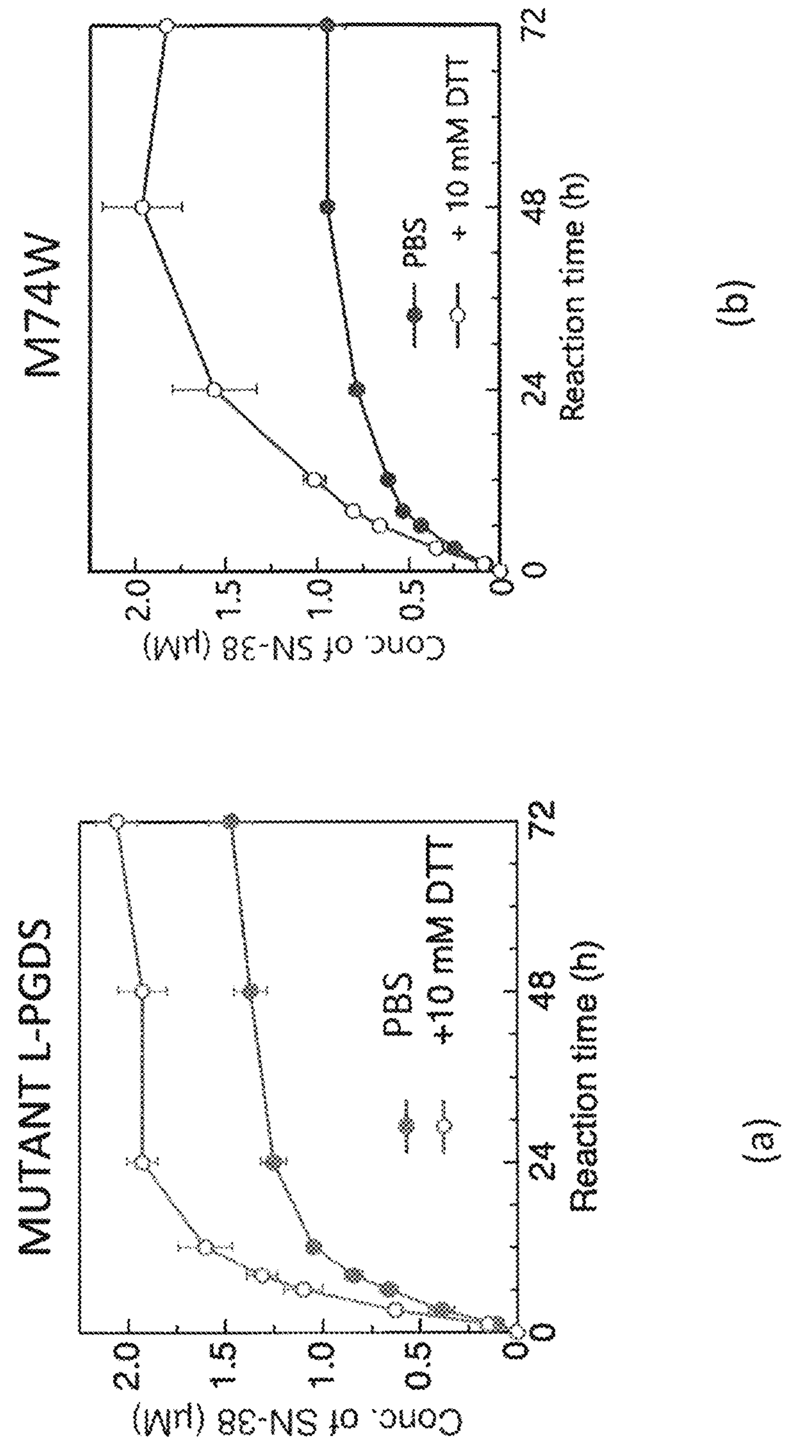
FIG. 9 is a graph showing the results of the studies on holding force and releasing capacity of capsule proteins (barrier-attached mutant) having SN-38 molecule loaded therein.

The same conditions as those of the above experiments applied to the experiments with the following "non-D-clip"

versions of the mutants as described above, i.e., the barrier-attached mutant ("M74W") and the mutant L-PGDS. The experiment for the mutant L-PGDS was a repeated experiment of that shown in FIG. 8. FIG. 9 shows the results. Specifically, FIGS. 9 (*a*) and (*b*) show the results for the mutant L-PGDS and the barrier-attached mutant (M74W), respectively. In FIGS. 9 (*a*) and (*b*), the horizontal axis represents reaction time (hr), and the vertical axis represents SN-38 concentration (μM).

Referring to FIG. 9(*a*), the concentration of SN-38 in the external PBS solution (solid circle or "●") was shown to have almost the same behavior as that shown in FIG. 8. This indicates that the findings in the experiment shown in FIG. 8 is reproducible. The studies for the mutant L-PGDS found that the concentration of SN-38 in the external DTT/PBS solution (open circle or "○") had reached 2.0 μM within shorter reaction time, and then almost a plateau early on.

Referring to FIG. 9(*b*), the concentration of SN-38 in the external solution PBS (solid circle or "●"), was not higher than 1.0 μM even at the end of the monitoring period. This shows that the barrier-attached mutant had suppressed the release of SN-38 as compared with the mutants shown in FIG. 8, that is, the mutant L-PGDS, the barrier-attached D-clip mutant or the targeting barrier-attached D-clip mutant.

The SN-38 concentration in the external DTT/PBS solution (open circle or "●") had reached approximately 2.0 μM even at the first 48 hours of dialysis. This value was substantially the same as the final concentrations of the barrier-attached D-clip and the targeting barrier-attached D-clip mutants shown in FIG. 8. In other words, those studies found that the barrier-attached mutant was superior in drug holding capacity to the barrier-attached D-clip mutant and the targeting barrier-attached D-clip mutant. The studies demonstrated that the reducing environments caused the release of the drugs encapsuled in the barrier-attached mutant, similar to those encapsulated in other capsule proteins.

Figure 10:
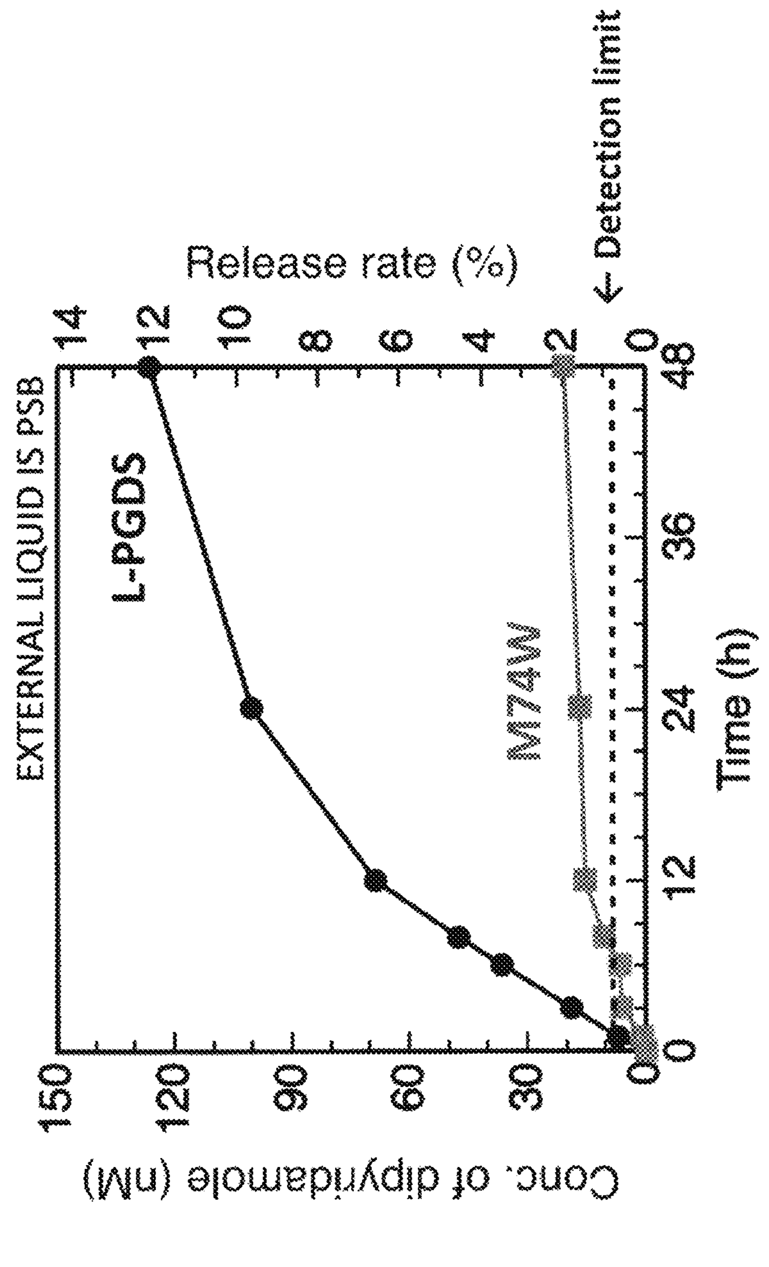
FIG. 10 is a graph showing the results of the studies on holding force of capsule proteins (barrier-attached mutants) having dipyridamole loaded therein.

FIG. 10 shows the results of the same experiments as described above, provided that dipyridamole was encapsulated instead of SN-38. Dipyridamole is a poorly water-soluble antianginal drug. The external solution was PBS. Referring to FIG. 10, the horizontal and the left vertical axes represent the reaction time (hr) and dipyridamole concentration (nM), respectively. In addition, the right vertical axis represents the release rate (%), or a value converted from the concentration on the left vertical axis. The dipyridamole concentration for the mutant L-PGDS increased over the reaction time, whereas that for the barrier mutant (M74W) increased only to the vicinity of the detection limit.

As described above, the barrier-attached mutant was found to have excellent retention capacity of the loaded drug, demonstrating that the mutant can retain some drugs almost without leakage. This means that the mutant would retain the drug encapsulated therein after administration to the subject and subsequence delivery therein, until the mutant reaches the reducing environment inside the cells, leading to highly efficient DDS.

<In-Vivo Effects>

Four-week-old male BALB/C-nu/nu mice (Japan SLC, Inc.) were housed and acclimatized for 1 week under free water supply and feeding in an animal room controlled on a 12-hour light-dark cycle at room temperature. Thereafter, 100 μL of human prostate cancer cells PC-3 at $5\times10^7$ cells/mL (PBS: Matrigel=1:1) was subcutaneously administered to right flank to prepare prostate cancer model mice.

The tumor volume was calculated from the following approximate expression: $(½)\times\{(\text{major axis})\times(\text{minor axis})^2\}$. When the tumor volume had reached 250 $mm^3$, Day 0 was set for administration to mice. The mice were randomly divided into groups as follows: PBS, SN-38/mutant L-PGDS at a dose of 2.0 mg/kg/d, SN-38/targeting mutant L-PGDS at a dose of 2.0 mg/kg/d, SN-38/barrier-attached D-clip mutant at a dose of 2.0 mg/kg/d, or SN-38/targeting barrier-attached D-clip mutant at a dose of 2.0 mg/kg/d were administered intravenously via tail vein every other day for 8 times in total. Mice in the control group were administered with PBS.

Figure 11:
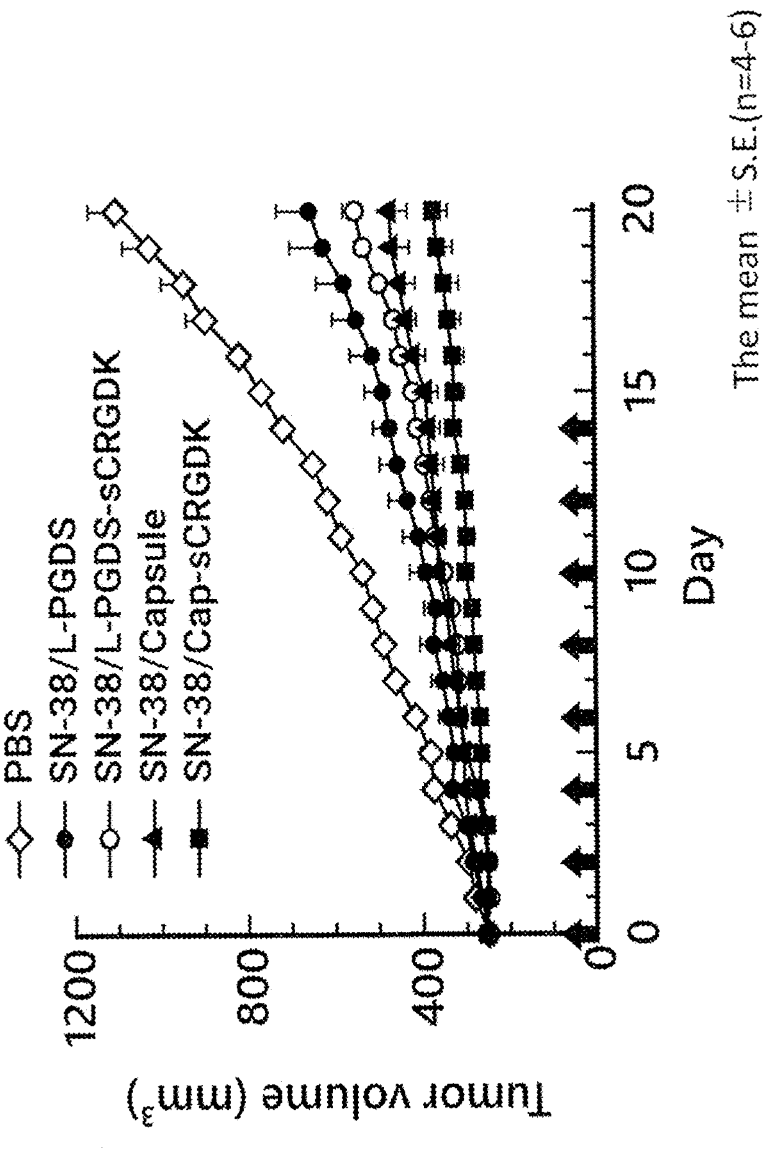
FIG. 11 is a graph showing the results of the studies on the ability of capsule proteins to suppress tumor growth when the SN-38-loaded capsule proteins were administered to mice carrying human prostate tumor cells.

FIG. 11 shows results of the in vivo experimental studies on anti-tumor activity. The horizontal axis represents the number of days elapsed from Day 0 of administration (days), and the vertical axis represents tumor volume ($mm^3$). Abbreviations in the graph are as follows:

PBS: control group

SN-38/L-PGDS: SN-38/mutant L-PGDS

SN-38/L-PGDS-sCRGDK: SN-38/targeting mutant L-PGDS

SN-38/Capsule: SN-38/barrier-attached D-clip mutant

SN-38/Cap-sCRGDK: targeting barrier-attached D-clip mutant

The PBS-administered group showed no anti-tumor activity. Specifically, the group showed a progressive increase in tumor volume, after the first administration of PBS. On the other hand, the SN-38/L-PGDS-, SN-38/L-PGDS-sCRGDK-, SN-38/Capsule-, and SN-38/Cap-sCRGDK-administered groups showed remarkable suppression of tumor growth.

In addition, the SN-38/Capsule- and SN-38/L-PGDS-sCRGDK-administered groups did not show significantly more efficient suppression of tumor growth than the SN-38/L-PGDS-administered group. These studies revealed that the addition of either targeting or release controlling function alone did not result in significantly much higher anti-tumor activity than the mutant L-PGDS.

On the other hand, SN-38/Cap-sCRGDK (targeting barrier-attached D-clip mutant) showed significantly higher anti-tumor activity than SN-38/L-PGDS (mutant L-PGDS). Those studies revealed that the two functions, i.e., the drug release controlling function (barrier amino acid and D-clip) and the tumor targeting function (targeting peptide), had achieved synergistic effects including significant suppression of tumor growth.

<Multimer>

The following describes preparation of a multimeric composition (e.g., octameric composition) of capsule proteins. As described in FIG. 5, the octameric composition has been assembled from four dimers 36, each of which includes two capsule proteins 34 bounded to each other via linker 35; and a tetramer 32 of streptavidin 30, to which the four dimers 36 are bound via biotin 38.

Therefore, an octameric composition of the capsule proteins was produced by the following steps: producing a biotinylated dimeric complex of two capsule proteins bound to a biotin; and assembling four sets of the biotinylated dimeric complexes and a tetramer of streptavidin separately produced to form the octameric composition. The linker is encoded by a nucleotide sequence shown in Table 7 (SEQ ID NO: 7). The streptavidin is also encoded by a nucleotide sequence shown in Table 8 (SEQ ID NO: 8).

TABLE 7

| SEQ ID NO: 7 Linker sequence | | | | | |
|---|---|---|---|---|---|
| 5 | 10 | 20 | 30 | 40 | 50 |
| GGGGS | | | | | |

TABLE 8

| SEQ ID NO: 8 Streptavidin | | | |
|---|---|---|---|
| GCTGAAGCTG | GTATCACCGC | CACCTGGTAC | AACCAGCTGG |
| GATCCACCTT | CATCGTTACC | GCTGGTGCTG | ACGGTGCTCT |
| GACCGGTACC | TACGAATCCG | CTGTTGGTAA | CGCTGAATCT |
| AGATACGTTC | TGACCGGTCG | TTACGACTCC | GCTCCGGCTA |
| CCGACGGTTC | CGGAACCGCT | CTGGGTTGGA | CCGTTGCTTG |
| GAAAAACAAC | TACCGTAACG | CTCACTCCGC | TACCACCTGG |
| TCTGGCCAGT | ACGTTGGTGG | TGCTGAAGCT | CGTATCAACA |
| CCCAGTGGTT | GTTGACCTCC | GGCACCACCG | AAGCCAACGC |
| GTGGAAATCC | ACCCTGGTTG | GTCACGACAC | CTTCACCAAA |
| GTTAAACCGT | CCGCTGCTTC | CCATCACCAT | CACCACCATT |
| AATAAAAGCT | TG | | |

<Preparation of Dimer L-PGDS Expression Vector>

PCR amplification was conducted using forward and reverse primers containing BamHI and EcoRI recognition sites, respectively, for preparation of the barrier-attached mutant gene sequence. The reverse primer further contained a linker sequence (GGGGS: SEQ ID NO: 7). The amplified products were then subjected to agarose gel electrophoresis, followed by restriction enzyme treatment using BamHI and EcoRI to prepare a barrier-attached mutant insert.

The barrier-attached mutant was designed to have the following substitutions. That is, this mutant was designed to include two alanine residues at positions 45 and 147 from N-terminus, instead of two cysteine (C) residues (i.e. this mutant has the same substitution as those of "C45A/C147A"), and to further include a tryptophan (W) residue as a barrier amino acid, instead of methionine (M) residue within D-strand at position 74 from the N-terminus of the mutant L-PGDS ("M74W"). Table 9 shows the amino acid sequence of the barrier-attached mutant (SEQ ID NO: 9).

TABLE 9

| SEQ ID NO: 9 Barrier-attached mutant | | | | |
|---|---|---|---|---|
| 10 | 20 | 30 | 40 | 50 |
| GSAPEAQVSV | QPNFQQDKFL | GRWFSAGLAS | NSSWLRE**K**KA | ALSMAKSVVA |
| 60 | 70 | ▲ 80 | 90 | 100 |
| PATDGGLNLT | STFLRKNQCE | TRTWLLQPAG | SLGSYSYRSP | **H**WGSTYSVSV |
| 110 | 120 | 130 | 140 | 150 |
| VETDYDQYAL | LYSQGSKGPG | EDFRMATLYS | RTQTPRAELK | EKFTAFAKAQ |
| 160 | 170 | | | |
| GFTEDTIVFL | PQTDKCMTEQ | | | |

In addition, a restriction enzyme-treated plasmid (pGEX4T-2) was similarly prepared. The barrier-attached mutant insert and the restriction treated pGEX4T-2 were separately subjected to agarose gel electrophoresis.

After ethidium bromide staining of the gels, Agarose Gel Extraction Kit (Jene Bioscience) was used for isolation of each of the DNA fragments followed by ligation. These operations had inserted into the pGEX4T-2 plasmid, the nucleotide sequence encoding the barrier-attached mutant bound to the linker. This plasmid is referred to as a barrier-attached mutant expression vector.

*E. coli* DH5α (DE3) strain was transformed using the barrier-attached mutant expression vector as described above, and inoculated into LB/Amp plate medium. Colonies grown in the plate medium were then subjected to Colony direct PCR. The colonies containing the barrier-attached mutant were inoculated into an LB/Amp test tube medium (5 mL) and cultured at 37° C. for 16 hours. Thereafter, a miniprep was done with SV Minipreps (promega) to purify the barrier-attached mutant expression vector.

Sequencing of the obtained barrier-attached mutant expression vector was performed to confirm insertion of the nucleotide sequence encoding the barrier-attached mutant and the linker.

The barrier-attached mutant insert had been amplified using primers containing EcoRI and SalI recognition sites. The mutant insert was then incorporated into the barrier-attached mutant expression vector by the same procedure as described above. Thereafter, *E. coli* DH5α (DE3) strain was transformed by the same procedure, cultured and amplified, and then the plasmid was purified. The plasmid contained a nucleotide sequence encoding the barrier-attached mutants that forms its dimer. Therefore, this plasmid is referred to as a dimeric barrier-attached mutant expression vector. The obtained dimeric barrier-attached mutant expression vector was subjected to sequencing to verify its nucleotide sequence authenticity.

<Preparation of Modified Dimer L-PGDS Expression Vector>

Complementary DNA oligonucleotides of SEQ ID NOs: 10 and 11 were annealed to have a unique15 amino acid residues (Avitag™, hereinafter called "Av"), specifically recognized by the biotin ligase (BirA). The biotin ligase conjugated a single biotin to a lysine residue of the peptide Av. Tables 10 and 11 show the nucleotide sequences of the primers. Thereafter, an annealed product was purified using a column for purification, FastGene Gel/PCR Extraction Kit (Nippon genetics, Tokyo). This nucleotide sequence is called an Av nucleotide sequence.

TABLE 10

| SEQ ID NO: 10 Av Sense primer (5' to 3') | | | |
|---|---|---|---|
| 10 | 20 | 30 | 40 |
| GTTCCGCGTG | GATCCATGTC | TGGCCTGAAC | GATATTTTCG |
| 50 | 60 | 66 70 | |
| AAGCGCAGAA | AATTGAATGG | CACGAA | |

TABLE 11

| SEQ ID NO: 11 Av Antisense primer (5' to 3') | | | |
|---|---|---|---|
| 10 | 20 | 30 | 40 |
| CTCGGGTGCG | GATCCTTCGT | GCCATTCAAT | TTTCTGCGCT |
| 50 | 60 | 66 70 | |
| TCGAAAATAT | CGTTCAGGCC | AGACAT | |

The dimeric barrier-attached mutant expression vector was subjected to restriction enzyme cleavage using BamHI (37° C., 3 hours), followed by agarose gel electrophoresis. Thereafter, DNA of the dimer barrier-attached mutant expression vector was extracted, and the Av nucleotide sequence was inserted at BamHI restriction site by In Fusion (Registered trademark) HD Cloning Kit (Clontech). The above dimeric barrier-attached mutant expression vector having the Av nucleotide sequence inserted therein is referred to as a modified dimeric barrier-attached mutant expression vector. The resulting vector was sequenced to confirm insertion of the target sequence.

<Dimer Barrier-Attached Mutant Expression Strain>

*E. coli* strain AVB101 expressing BirA was transformed with the modified dimeric barrier-attached mutant expression vector to obtain a dimeric barrier-attached mutant-expressing strain. The dimeric barrier-attached mutant-expressing strain was inoculated into 5 ml of an LB/Amp/Chl liquid medium and cultured with shaking overnight at 37° C. The strain was then transferred to 1 L of 2×YT/Amp/Chl medium and cultured at 37° C.

The BirA-expressing *E. coli* strain AVB101 was an *E. coli* strain that had been injected with an expression vector including the BirA coding nucleotide sequence.

<Production of Biotinylated Dimer Barrier-Attached Mutant>

When OD 600 value of the culture medium of the dimeric barrier-attached mutant-expressing strain reached 0.6 to 1.0, IPTG and biotin were added to the final concentrations of 0.1 mM and 50 μM, respectively. The operation led to expressions in *E. coli* of both of the above proteins, i.e., the modified dimer barrier-attached mutant and BirA. Then, BirA conjugated a single biotin to a peptide Av incorporated in the dimeric barrier-attached mutant. The processes led to biotinylation of the dimeric barrier-attached mutant.

Thereafter, the strain was cultured at 37° C. for 6 hours, and the culture solution was centrifuged (8,400×g, 10 min, 4° C.) to recover bacterial cells. Further, the bacterial cells were washed with PBS and collected by centrifugation, and the bacterial cells were ultrasonically disrupted.

The affinity column, into which 15 ml of Glutathione Sepharose 4B (GE Helthcare Bio Science, UK) medium had been dispensed, was equilibrated with 5 column volumes of PBS that had passed through a 0.22 μm filter. The disruption supernatant passed through a 0.22 μm filter and was subjected to the affinity column.

After the column was washed with 3 column volumes of 1% Triton X-100/PBS and 5 column volumes of PBS, 165 units of thrombin (SIGMA) was added thereto, and the mixture was well stirred and allowed to stand at room temperature for 12 hours or more. The fraction containing target molecules was eluted with 5 column volumes of PBS, repeatedly centrifuged (8,400 g, 20 min, 4° C.) using an Amicon® device with 10 kDa molecular weight cutoff (MWCO) and concentrated to 4 ml.

Subsequently, 5 mM Tris-HCl (pH 8.0) passed through a 0.22 μm filter was degassed for 10 minutes, and Superdex 75 16/600 (GE Helthcare Bio Science, UK) was equilibrated with 2 column volumes of the same buffer. The above concentrate was passed through a 0.22 μm filter and added to the aforementioned Superdex 75 16/600. Eluate was fractionated by 1.5 ml at a flow rate of 0.5 ml/min while monitoring absorbance at an ultraviolet wavelength of 280 nm, and the fractions of a peak corresponding to the biotinylated dimer L-PGDS were collected.

The collected fractions were pooled and dialyzed against 20 mM Sodium acetate buffer solution (pH 5.5), then repeatedly centrifuged (8,400 g, 20 min, 4° C.) using an Amicon® device with 10 kDa MWCO, and concentrated to 4 ml.

Cation exchange chromatography was conducted using a column packed with SP sepharose Fast Flow (GE Healthcare Bio Science, UK) and an linear gradient between 20 mM sodium acetate buffer (pH5.5) and 1M NaCl/20 mM sodium acetate buffer (pH5.5).

Eluate was fractionated by 1.5 ml at a flow rate of 1.0 ml/min while monitoring absorbance at an ultraviolet wavelength of 280 nm. Thereafter, SDS-PAGE analysis was performed to collect a fraction in which a single band of the biotinylated dimer barrier-attached mutant was identified.

<Purification of Streptavidin>

*E. coli* BL21 (DE3) strain was transformed with a streptavidin expression vector (pET21a-Streptavidin-Alive, Addgene) to obtain a streptavidin-expressing strain. The streptavidin-expressing strain was inoculated into 5 ml of an LB/Amp liquid medium and cultured with shaking overnight at 37° C. The strain was then transferred to 1 L of 2×YT/Amp medium and cultured at 37° C. Thereafter, when the OD600 value reached 0.6 to 1.0, IPTG was added so as to have a final concentration of 0.1 mM to induce expression. Further, after culturing at 18° C. for 24 hours, the culture solution was centrifuged (8,400×g, 10 min, 4° C.) to recover bacterial cells.

The obtained bacterial cells were suspended in PBS, and 1 μl of 100 mg/ml lysozyme was added per 1 g of the bacterial cells, and the mixture was stirred in ice cold bath. Further, the bacterial cells were ultrasonically disrupted (7 sets of 1 minute sonication and 2 minutes rest) using stirring in ice cold bath, and the disrupted solution was subjected to centrifugation (4° C., 15,000 rpm) to extract a supernatant fluid.

Subsequently, the supernatant fluid was subjected to an affinity column as follows. Specifically, 10 ml of Ni sepharose (GE Helthcare Bio Science, UK) had been dispensed into the column, and equilibrated with 5 column volumes of 20 mM imidazole/20 mM sodium phosphate buffer (pH 7.0), which had been pretreated with passing through a 0.22 μm filter. The washing was conducted with 20 mM sodium phosphate buffer (pH 7.0) and various concentrations of imidazole (20, 50,and 100 mM). The elution was conducted with 300 mM imidazole/sodium phosphate buffer (pH 7.0). Thereafter, the resulting eluate was repeatedly centrifuged (8,400 g, 20 min, 4° C.) using an Amicon® device with 10 kDa MWCO, and concentrated to 4 ml.

PBS (pH 7.4) passed through a 0.22 μm filter was then degassed for 10 minutes, and Superdex 75 16/600 was equilibrated with 2 column volumes of the same buffer. The above concentrate was passed through a 0.22 μm filter and added to the Superdex 75 16/600 column. Eluate was fractionated by 1.5 ml at a flow rate of 0.5 ml/min while monitoring absorbance at an ultraviolet wavelength of 280 nm, and a streptavidin tetramer was obtained by non-reducing SDS-PAGE analysis.

<Preparation of Octameric Composition>

PBS solutions of purified dimer barrier-attached mutant (pH 7.4) and streptavidin tetramer (pH 7.4) were mixed at a molar ratio of 4:1, and the mixture was allowed to stand at room temperature for 15 minutes. Thereafter, the eluate was repeatedly centrifuged (8,400 g, 20 min, 4° C.) using Amicon® device with 50 kDa MWCO, and concentrated to 4 ml.

Next, PBS (pH 7.4) passed through a 0.22 μm filter was degassed for 10 minutes, and Superdex 200 16/600 (GE Helthcare Bio Science, UK) was equilibrated with 2 column volumes of the same buffer. The concentrate was passed through a 0.22 μm filter and added to Superdex 200 16/600. Eluate was fractionated by 1.5 ml at a flow rate of 0.5 ml/min while monitoring absorbance at an ultraviolet wavelength of 280 nm, and an octameric composition was obtained by SDS-PAGE analysis.

Monomers of the barrier-attached mutant were produced through transformation of *E. coli* with the barrier-attached mutant expression vector, which had been used for preparation of the dimeric barrier-attached mutant expression vector. In addition, monomers of a targeting barrier-attached mutant including iRGD peptide were also prepared. The amino acid sequence of the targeting barrier-attached mutant (SEQ ID NO: 12) is shown in Table 12. The method of adding an iRGD peptide is the same as in the case of SEQ ID NO: 6.

TABLE 12

SEQ ID NO: 12 Labeled barrier-attached mutant

| 10 | 20 | 30 | 40 | 50 |
|---|---|---|---|---|
| GSAPEAQVSV | QPNFQQDKFL | GRWFSAGLAS | NSSWLRE**K**KA | ALSMAKSVVA |
| 60 | 70 | ▲ 80 | 90 | 100 |
| PATDGGLNLT | STFLRKNQCE | TRTWLLQPAG | SLGSYSYRSP | **H**WGSTYSVSV |
| 110 | 120 | 130 | 140 | 150 |
| VETDYDQYAL | LYSQGSKGPG | EDFRMATLYS | RTQTPRAELK | EKFTAFAKAQ |
| 160 | 170 | ■ | | |
| GFTEDTIVFL | PQTDK**CRGDK** | **GPDC** | | |

Also, a tetrameric composition including four monomers of the capsule proteins bound to a streptavidin can be obtained by transforming an BirA-expressing *E. coli* AVB101 strain with the modified monomer barrier-attached mutant expression vector, in which an Av nucleotide sequence is inserted into the barrier-attached mutant expression vector.

<Size of Octameric Composition>

<Size of Octameric Composition by DLS>

<Size Measurement of Octamer by SAXS>

Size of the obtained octameric composition was measured by small-angle X-ray scattering (SAXS). For comparison, size of the mutant L-PGDS was also measured.

SAXS data collection was carried out at BL40B2, a beamline in the SPring-8 synchrotron radiation facility (Sayo-gun, Hyogo). The X-ray wavelength was tuned to 1.000 A (angstrom), the sample-to-detector distance was set to 2.193 m, and the experiments were performed at 25° C. The exposure times for each measurement were 20 to 50 s. Scattering intensity was recorded with PILATUS-2M (RIGAKU, Tokyo) as a detector.

A sample cell with a thickness of 3.0 mm was used to maximize scattering of X-ray. The windows of the cell were made of 0.02 mm thick quartz plates. To avoid systematic errors, the inventor measured the sample (protein) and buffer solutions alternately. 25 μL of a sample solution was placed in the cell for its data collection. The solution was removed from the cell; and the cell was then washed 3 times with a buffer solution before data collection of the next sample solution.

Two-dimensionally recorded scattering patterns of the protein sample and the buffer solutions were transformed to a one-dimensional profile by circular averaging. Contributions to scattering intensities from the solvent were eliminated from the raw data of the sample solutions by subtracting the intensity profile obtained for the buffer solution. Scattering profiles in the small-angle region were analyzed by Guinier's approximation for monodispersive systems: The scattering intensity (I (S,C)) as a function of reciprocal vector (S) and protein concentration (C), is expressed by the forward scattering intensity (I(0,C)) and the radius of gyration $R_g(C)$ (See the following formula (1)).

[Mathmatical formula 1]

$$I(S, C) = I(0, C)\exp\left[-\frac{4}{3}\pi^2 \times R_g(C)^2 S^2\right] \quad (1)$$

$$\text{wherein } S = \frac{2\sin\theta}{\lambda}$$

wherein, 2θ represents the scattering angle relative to the incident beam, and λ represents the X-ray wavelength.

The radius of gyration $R_g$ for each sample solution was calculated from Guinier region in its scattering profile. The radius of gyration $R_g$ for the monomer (mutant L-PGDS) was 1.8±0.04 nm, whereas the $R_g$ for the octameric composition, 6.0±0.69 nm was about 3 times that of the monomer. These results revealed that the octamerization has increased the radius of gyration $R_g$. Table 13 summarizes results of the experiments. This table indicates that experimental values of molecular weights ($Mw^{exp}$) from the scattering profiles of the monomer (mutant L-PGDS) and the octameric composition were close to their respective theoretical values ($Mw^{calc}$). This demonstrates that the monomers (mutant L-PGDS), each of which has the same molecular weight, have formed an octamer as barrier mutant. The overall size of the composition was found to exceed 10 nm as described above, indicating that the octameric composition can be expected to accumulate in tumors owing to EPR effect.

TABLE 13

| | $R_g$(nm) | $D_{max}$ (nm) | $Mw^{exp}$(kDa) | $Mw^{calc}$(kDa) |
|---|---|---|---|---|
| Monomer | 1.8 ± 0.04 | 4.75 | 16 | 19 |
| Octamer composition | 6.0 ± 0.69 | 22.4 | 231 | 217 |

<Drug Encapsulation>

Encapsulation of SN-38 was carried out in the monomer, the barrier-attached mutant, the targeting barrier-attached mutant, or the octameric composition. SN-38 is an abbreviation for 7-ethyl-10-hydroxycamptothecin, which is a poorly water-soluble anticancer drug, as already described. The compound is known to show a high anti-tumor effect at a lower dose compared with irinotecan hydrochloride, a current choice of a clinically used prodrug of SN-38.

To a PBS suspension of SN-38 incubated at 37° C., a PBS solution of a monomer (mutant L-PGDS), a barrier-attached mutant, a targeting barrier-attached mutant or an octameric composition was added to have the final concentrations of 1 μM, 0.25 μM and 0.125 μM. The mixtures were stirred at 37° C. for 6 hours. After completion of stirring, free SN-38 molecules were removed by ultrafiltration to prepare a sample containing a drug in the capsule protein.

<In-Vivo Effects>

Four-week-old male BALB/C-nu/nu mice (Japan SLC) were housed and acclimatized for 1 week under free water supply and feeding in an animal room controlled on a 12-hour light-dark cycle at room temperature. Thereafter, 100 μL of human prostate cancer cells PC-3 at $5\times10^7$ cells/mL (PBS: Matrigel=1:1) was subcutaneously administered to right flank to prepare prostate cancer model mice.

The tumor volume was calculated from the following approximate expression: (½)×{(major axis)×(minor axis)$^2$}, When the tumor volume had reached 250 mm$^3$, Day 0 was set for administration to mice. The mice were randomly divided into groups as follows: PBS, the monomer at a dose of 2.0 mg SN-38/kg/d, the barrier-attached mutant at a dose of 2.0 mg SN-38/kg/d, the targeting barrier-attached mutant at a dose of 2.0 mg SN-38/kg/d), and the octameric composition at a dose of 2.0 mg SN-38/kg/d) were administered via tail vein every 4 days for 4 times in total. For the control group, only PBS was administered every 4 days for four times in total.

Figure 12:
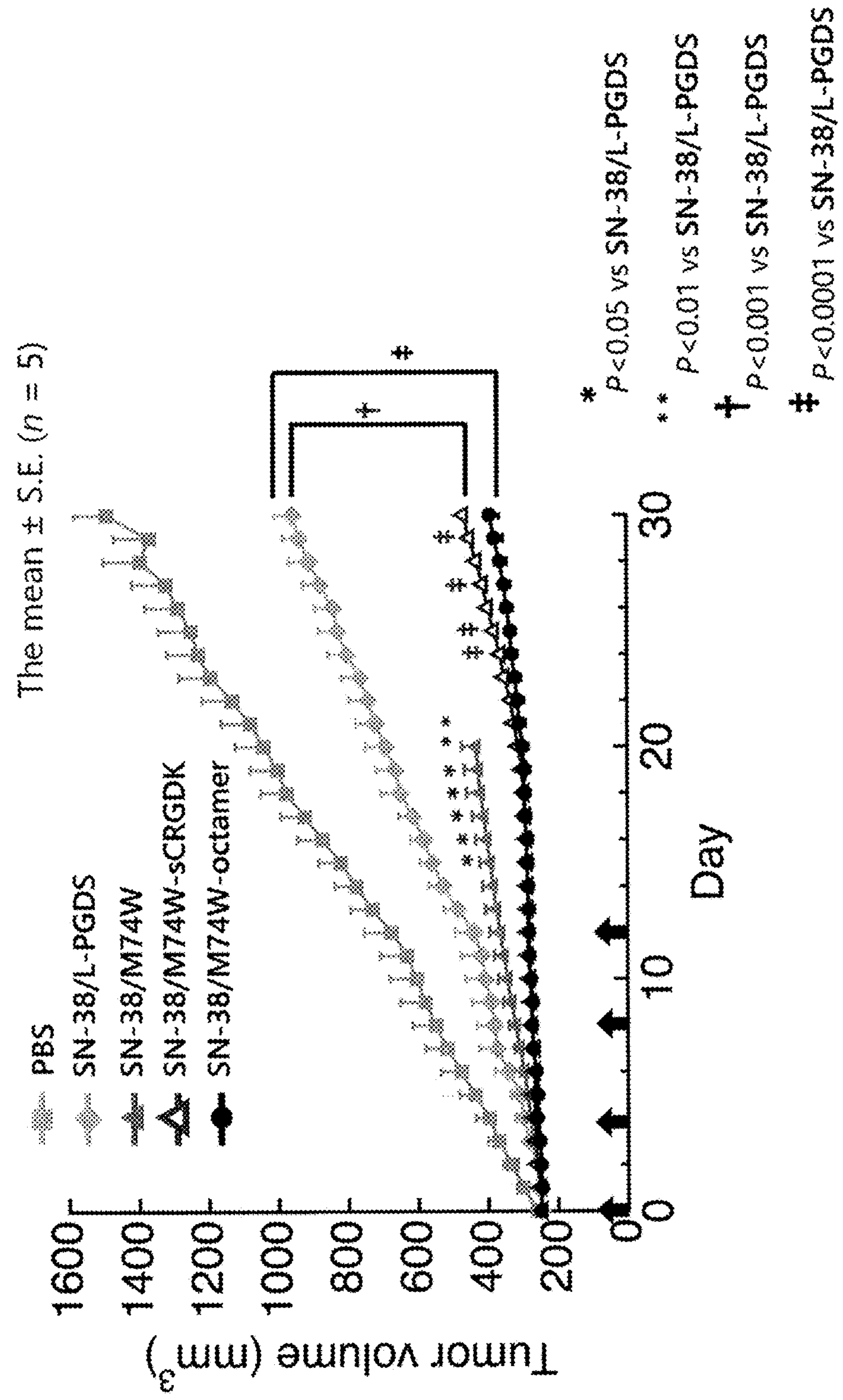
FIG. 12 is a graph showing the results of the studies on the ability of capsule proteins to suppress tumor growth when octameric compositions of SN-38-loaded capsule proteins were administered to mice carrying human prostate tumor cells.

FIG. 12 shows results of the in vivo experimental studies on anti-tumor activity. The horizontal axis represents the number of days elapsed from Day 0 of administration (days), and the vertical axis represents tumor volume (mm$^3$). Abbreviations in the graph are as follows:

PBS: control group

SN-38/L-PGDS: monomer (SN-38/mutant L-PGDS)

SN-38/M74W: SN-38/barrier-attached mutant

SN-38/M74W-sCRGDK: SN-38/targeting barrier-attached mutant

SN-38/M74W-octamer: SN-38/octameric composition of barrier-attached mutant

All the mutants as described above has no D-clip while some of those described in FIG. 11 have D-clip.

The targeting barrier-attached mutant was obtained by adding a Cys-Arg-Gly-Asp-Lys (CRGDK) motif that recognizes Neuropilin-1 to C-terminus of the barrier-attached mutant (label number 12).

Referring to FIG. 12, the PBS-administered group showed no anti-tumor activity. Specifically, the group showed a progressive increase in the tumor volume, after the first administration of PBS solution. On the other hand, the SN-38/L-PGDS-administered group showed tumor suppression effect. Furthermore, the barrier-attached mutant SN-38/M74W further suppressed tumor growth.

On the other hand, with SN-38/M74W-sCRGDK (targeting barrier-attached mutant (no D-clip)) and SN-38/M74W-octamer (octameric composition of barrier mutant), surprisingly, almost no tumor growth was observed from the start of the experiment. In light of the fact that SN-38 itself is an anti-tumor drug rather than apoptosis-inducing agent, the studies described above demonstrated that the intrinsic effects of SN-38 were fully affected.

Further, with a total of four doses of the compositions every four days, tumor growth was completely suppressed not only within the administration period, but also at Day 15 or later (dose free period). This demonstrates that the pharmaceutical agents remained in the cell tissues with no excretion by the lymphatic system or the like, to achieve prolonged pharmaceutical actions owing to EPR effect.

Figure 13:
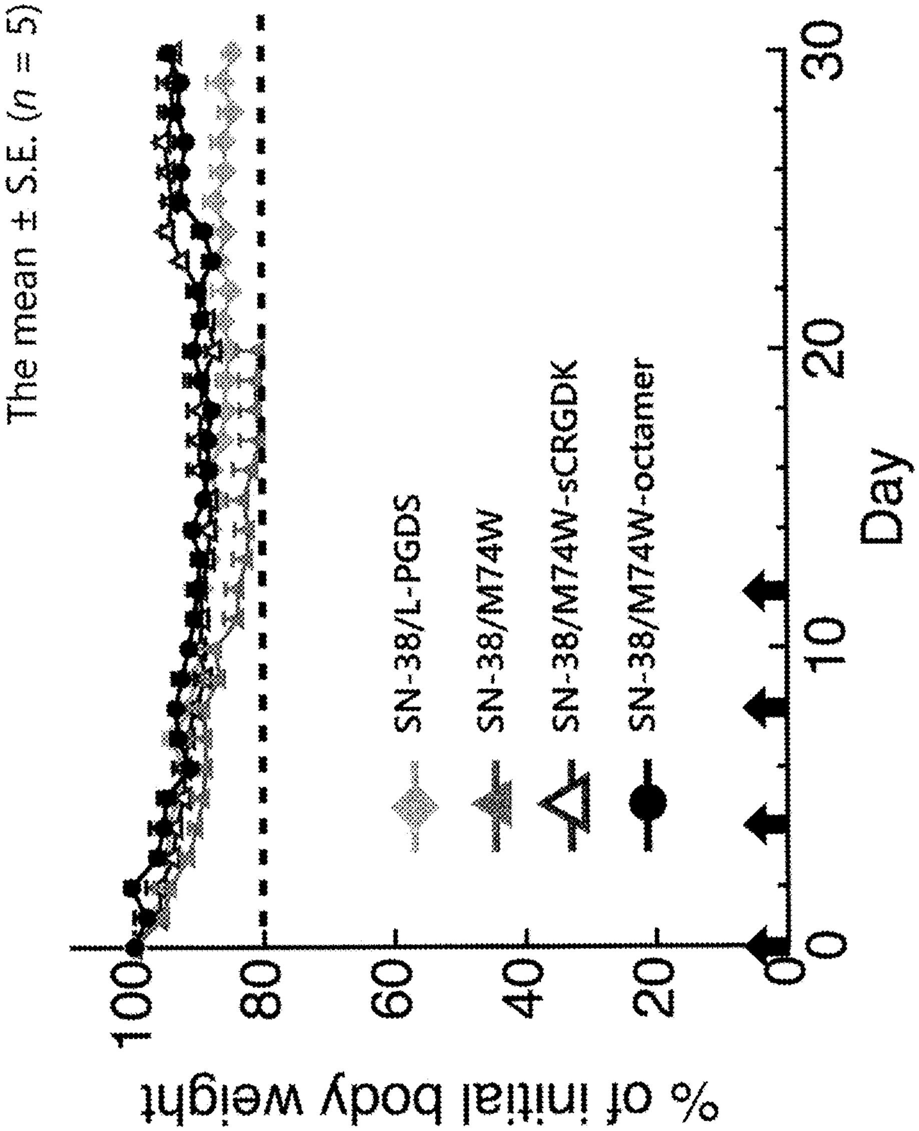
FIG. 13 is a graph showing weight changes of the mice in FIG. 12.

FIG. 13 shows average body weight of mice when the experiment of FIG. 12 was performed. The horizontal axis represents the number of days elapsed from Day 0 of administration (days), and the vertical axis represents body weight ratio (%), i.e., the body weight measured in days after the initial administration to the body weight at the start of administration. The values shown for each compound-administered group (5 mice) represent the mean for the group. Abbreviations in the graph are the same as those in FIG. 12. The PBS-administered group, which is the control group in FIG. 12, is not shown in FIG. 13.

Although the barrier-attached mutant showed effective suppression of tumor cell growth as previously described, as shown in FIG. 13, "SN-38/M74W"-administered group showed signs of dropping below 80% of body weight on Day 20, and the experiment was interrupted. In light of the fact that "SN-38/L-PGDS"-administered group also showed weight loss but not below 80% and that L-PGDS used for administration to the group merely had lost its enzymatic activity; the barrier-attached mutant was excellent in retaining the encapsulated drug (SN-38), but some of the loaded drug was also released even in normal cells, which may have caused the adverse effects.

On the other hand, "SN-38/M74W-sCRGDK"- and "SN-38/M74W-octamer"-administered groups showed a slight body weight loss, and even a tendency to increase after Day 15, on which no additional SN-38 was administered. As described previously, the proteins used in administration to the two groups, that is, the targeting barrier-attached mutant and the octamer of the barrier mutant per se showed a remarkably effective suppression of tumor cell growth.

The above studies found that the targeting barrier-attached mutant (SN-38/M74W-sCRGDK) and the octamer of the barrier mutant (SN-38/M74W-octamer) specifically distinguished cancer cells and released the drug in the cancer cells.

In addition, when the EPR effect is exhibited by forming a multimer, a drug can be delivered regardless of tumor types. Especially for metastatic cancer, embodiments of the present capsule proteins enable drugs selectively delivered to cancer cells without affecting normal cells regardless of the location of metastasis, and thus it is considered to be very useful.

INDUSTRIAL APPLICABILITY

The present invention encapsulates compounds such as poorly soluble drugs to become soluble. Once the encapsulated compounds are intracellularly delivered, the encapsulant will release the compounds in the intracellular reducing environment, with disulfide bond cleavage on the encapsulant. The intracellular concentration of reduced glutathione, ca. 0.5 mM to 10 mM is 100 to 1000 times higher than the extracellular concentration. Therefore, an embodiment of the present invention will provide a DDS capsule used for a poorly soluble compound. Furthermore, the solubilization technology of poorly soluble substances can be applied to industrial products and industrial materials other than drugs.

REFERENCE SIGNS LIST

10 open mouth (of barrel structure)
12 disulfide clip
14 gap
21 multimeric composition (octameric composition)
22 multimeric composition (tetramer composition)
30 streptavidin
32 tetramer
35 linker
34 capsule protein
36 dimer
38 biotin

The invention claimed is:

1. A capsule protein including a mutant of the human lipocalin-type prostaglandin D synthase of SEQ ID NO: 1, wherein the synthase as substitution of alanine (A) for cysteine (C), at the active center of the synthase; and wherein at least one amino acid in β-strand D of the synthase, corresponding to position 68 to 78 of SEQ ID NO: 1, is substituted with lysine (K), histidine (H), tryptophan (W), tyrosine (Y), or phenylalanine (F).

2. The capsule protein according to claim 1, wherein a disulfide bond has been introduced between E-F loop and α-helix H2.

3. The capsule protein according to claim 1, wherein a cell targeting peptide is bound to N-terminus or C-terminus of the capsule protein and wherein the cell targeting peptide is selected from the group consisting of (i) Asn-Gly-Arg, (ii) Arg-Gly-Asp, (iii) Cys-Arg-Gly-Asp-Lys, (iv) Lys-Leu-Pro, (v) Asn-Val-Val-Arg-Gln, and (vi) Phe-Gln-His-Pro-Ser-Phe-Ile.

4. A multimeric composition containing a plurality of capsule proteins, each of the capsule proteins is the capsule protein according to claim 1.

5. The multimeric composition of a capsule protein according to claim 4, wherein the multimeric composition is a tetramer or an octamer.

6. The multimeric composition of a capsule protein according to claim 5, wherein the capsule protein is bound to a tetramer of streptavidin via biotin in the multimeric composition.

7. A pharmaceutical composition comprising a drug in the capsule protein according to claim 1.

8. The pharmaceutical composition according to claim 7, wherein the composition is lyophilized.

9. A processed food comprising a complex having non-drug compound contained in the capsule protein according to claim 1.

* * * * *

SEQUENCE LISTING

<160> NUMBER OF SEQ ID NOS: 12

<210> SEQ ID NO 1
<211> LENGTH: 168
<212> TYPE: PRT
<213> ORGANISM: Human

<400> SEQUENCE: 1

Ala Pro Glu Ala Gln Val Ser Val Gln Pro Asn Phe Gln Gln Asp Lys
1 5 10 15

Phe Leu Gly Arg Trp Phe Ser Ala Gly Leu Ala Ser Asn Ser Ser Trp
20 25 30

Leu Arg Glu Lys Lys Ala Ala Leu Ser Met Cys Lys Ser Val Val Ala
35 40 45

Pro Ala Thr Asp Gly Gly Leu Asn Leu Thr Ser Thr Phe Leu Arg Lys
50 55 60

Asn Gln Cys Glu Thr Arg Thr Met Leu Leu Gln Pro Ala Gly Ser Leu
65 70 75 80

Gly Ser Tyr Ser Tyr Arg Ser Pro His Trp Gly Ser Thr Tyr Ser Val
85 90 95

Ser Val Val Glu Thr Asp Tyr Asp Gln Tyr Ala Leu Leu Tyr Ser Gln
100 105 110

Gly Ser Lys Gly Pro Gly Glu Asp Phe Arg Met Ala Thr Leu Tyr Ser
115 120 125

Arg Thr Gln Thr Pro Arg Ala Glu Leu Lys Glu Lys Phe Thr Ala Phe
130 135 140

Cys Lys Ala Gln Gly Phe Thr Glu Asp Thr Ile Val Phe Leu Pro Gln
145 150 155 160

Thr Asp Lys Cys Met Thr Glu Gln
165

<210> SEQ ID NO 2
<211> LENGTH: 170
<212> TYPE: PRT
<213> ORGANISM: Artificial Sequence
<220> FEATURE:
<223> OTHER INFORMATION: Enzyme inactivation Mutant

<400> SEQUENCE: 2

Gly Ser Ala Pro Glu Ala Gln Val Ser Val Gln Pro Asn Phe Gln Gln
1 5 10 15

Asp Lys Phe Leu Gly Arg Trp Phe Ser Ala Gly Leu Ala Ser Asn Ser
20 25 30

Ser Trp Leu Arg Glu Lys Lys Ala Ala Leu Ser Met Ala Lys Ser Val
35 40 45

Val Ala Pro Ala Thr Asp Gly Gly Leu Asn Leu Thr Ser Thr Phe Leu
50 55 60

Arg Lys Asn Gln Cys Glu Thr Arg Thr Met Leu Leu Gln Pro Ala Gly
65 70 75 80

Ser Leu Gly Ser Tyr Ser Tyr Arg Ser Pro His Trp Gly Ser Thr Tyr
85 90 95

Ser Val Ser Val Val Glu Thr Asp Tyr Asp Gln Tyr Ala Leu Leu Tyr
100 105 110

Ser Gln Gly Ser Lys Gly Pro Gly Glu Asp Phe Arg Met Ala Thr Leu
115 120 125

Tyr Ser Arg Thr Gln Thr Pro Arg Ala Glu Leu Lys Glu Lys Phe Thr
130 135 140

```
Ala Phe Ala Lys Ala Gln Gly Phe Thr Glu Asp Thr Ile Val Phe Leu
145                 150                 155                 160

Pro Gln Thr Asp Lys Cys Met Thr Glu Gln
                165                 170


<210> SEQ ID NO 3
<211> LENGTH: 9
<212> TYPE: PRT
<213> ORGANISM: Artificial Sequence
<220> FEATURE:
<223> OTHER INFORMATION: iRGD peptide

<400> SEQUENCE: 3

Cys Arg Gly Asp Lys Gly Pro Asp Cys
1               5


<210> SEQ ID NO 4
<211> LENGTH: 174
<212> TYPE: PRT
<213> ORGANISM: Artificial Sequence
<220> FEATURE:
<223> OTHER INFORMATION: Signed Mutant

<400> SEQUENCE: 4

Gly Ser Ala Pro Glu Ala Gln Val Ser Val Gln Pro Asn Phe Gln Gln
1               5                   10                  15

Asp Lys Phe Leu Gly Arg Trp Phe Ser Ala Gly Leu Ala Ser Asn Ser
            20                  25                  30

Ser Trp Leu Arg Glu Lys Lys Ala Ala Leu Ser Met Ala Lys Ser Val
        35                  40                  45

Val Ala Pro Ala Thr Asp Gly Gly Leu Asn Leu Thr Ser Thr Phe Leu
    50                  55                  60

Arg Lys Asn Gln Cys Glu Thr Arg Thr Met Leu Leu Gln Pro Ala Gly
65                  70                  75                  80

Ser Leu Gly Ser Tyr Ser Tyr Arg Ser Pro His Trp Gly Ser Thr Tyr
                85                  90                  95

Ser Val Ser Val Val Glu Thr Asp Tyr Asp Gln Tyr Ala Leu Leu Tyr
            100                 105                 110

Ser Gln Gly Ser Lys Gly Pro Gly Glu Asp Phe Arg Met Ala Thr Leu
        115                 120                 125

Tyr Ser Arg Thr Gln Thr Pro Arg Ala Glu Leu Lys Glu Lys Phe Thr
    130                 135                 140

Ala Phe Ala Lys Ala Gln Gly Phe Thr Glu Asp Thr Ile Val Phe Leu
145                 150                 155                 160

Pro Gln Thr Asp Lys Cys Arg Gly Asp Lys Gly Pro Asp Cys
                165                 170


<210> SEQ ID NO 5
<211> LENGTH: 170
<212> TYPE: PRT
<213> ORGANISM: Artificial Sequence
<220> FEATURE:
<223> OTHER INFORMATION: Barrier D-clip Mutant

<400> SEQUENCE: 5

Gly Ser Ala Pro Glu Ala Gln Val Ser Val Gln Pro Asn Phe Gln Gln
1               5                   10                  15

Asp Lys Phe Leu Gly Arg Trp Phe Ser Ala Gly Leu Ala Ser Asn Ser
            20                  25                  30
```

-continued

```
Ser Trp Leu Arg Glu Cys Lys Ala Ala Leu Ser Met Ala Lys Ser Val
        35                  40                  45

Val Ala Pro Ala Thr Asp Gly Gly Leu Asn Leu Thr Ser Thr Phe Leu
    50                  55                  60

Arg Lys Asn Gln Cys Glu Thr Arg Thr Trp Leu Leu Gln Pro Ala Gly
65                  70                  75                  80

Ser Leu Gly Ser Tyr Ser Tyr Arg Ser Pro Cys Trp Gly Ser Thr Tyr
                85                  90                  95

Ser Val Ser Val Val Glu Thr Asp Tyr Asp Gln Tyr Ala Leu Leu Tyr
            100                 105                 110

Ser Gln Gly Ser Lys Gly Pro Gly Glu Asp Phe Arg Met Ala Thr Leu
        115                 120                 125

Tyr Ser Arg Thr Gln Thr Pro Arg Ala Glu Leu Lys Glu Lys Phe Thr
    130                 135                 140

Ala Phe Ala Lys Ala Gln Gly Phe Thr Glu Asp Thr Ile Val Phe Leu
145                 150                 155                 160

Pro Gln Thr Asp Lys Cys Met Thr Glu Gln
                165                 170
```

<210> SEQ ID NO 6
<211> LENGTH: 174
<212> TYPE: PRT
<213> ORGANISM: Artificial Sequence
<220> FEATURE:
<223> OTHER INFORMATION: Signed Barrier D-clip Mutant

<400> SEQUENCE: 6

```
Gly Ser Ala Pro Glu Ala Gln Val Ser Val Gln Pro Asn Phe Gln Gln
1               5                   10                  15

Asp Lys Phe Leu Gly Arg Trp Phe Ser Ala Gly Leu Ala Ser Asn Ser
            20                  25                  30

Ser Trp Leu Arg Glu Cys Lys Ala Ala Leu Ser Met Ala Lys Ser Val
        35                  40                  45

Val Ala Pro Ala Thr Asp Gly Gly Leu Asn Leu Thr Ser Thr Phe Leu
    50                  55                  60

Arg Lys Asn Gln Cys Glu Thr Arg Thr Trp Leu Leu Gln Pro Ala Gly
65                  70                  75                  80

Ser Leu Gly Ser Tyr Ser Tyr Arg Ser Pro Cys Trp Gly Ser Thr Tyr
                85                  90                  95

Ser Val Ser Val Val Glu Thr Asp Tyr Asp Gln Tyr Ala Leu Leu Tyr
            100                 105                 110

Ser Gln Gly Ser Lys Gly Pro Gly Glu Asp Phe Arg Met Ala Thr Leu
        115                 120                 125

Tyr Ser Arg Thr Gln Thr Pro Arg Ala Glu Leu Lys Glu Lys Phe Thr
    130                 135                 140

Ala Phe Ala Lys Ala Gln Gly Phe Thr Glu Asp Thr Ile Val Phe Leu
145                 150                 155                 160

Pro Gln Thr Asp Lys Cys Arg Gly Asp Lys Gly Pro Asp Cys
                165                 170
```

<210> SEQ ID NO 7
<211> LENGTH: 5
<212> TYPE: PRT
<213> ORGANISM: Artificial Sequence
<220> FEATURE:
<223> OTHER INFORMATION: Linker

<400> SEQUENCE: 7

-continued

```
Gly Gly Gly Gly Ser
1               5


<210> SEQ ID NO 8
<211> LENGTH: 412
<212> TYPE: DNA
<213> ORGANISM: Streptomyces avidinii

<400> SEQUENCE: 8

gctgaagctg gtatcaccgg cacctggtac aaccagctgg gatccacctt catcgttacc      60

gctggtgctg acggtgctct gaccggtacc tacgaatccg ctgttggtaa cgctgaatct     120

agatacgttc tgaccggtcg ttacgactcc gctccggcta ccgacggttc cggaaccgct     180

ctgggttgga ccgttgcttg gaaaaacaac taccgtaacg ctcactccgc taccacctgg     240

tctggccagt acgttggtgg tgctgaagct cgtatcaaca cccagtggtt gttgacctcc     300

ggcaccaccg aagccaacgc gtggaaatcc accctggttg gtcacgacac cttcaccaaa     360

gttaaaccgt ccgctgcttc ccatcaccat caccaccatt aataaaagct tg             412


<210> SEQ ID NO 9
<211> LENGTH: 170
<212> TYPE: PRT
<213> ORGANISM: Artificial Sequence
<220> FEATURE:
<223> OTHER INFORMATION: Barrier Mutant

<400> SEQUENCE: 9

Gly Ser Ala Pro Glu Ala Gln Val Ser Val Gln Pro Asn Phe Gln Gln
1               5                   10                  15

Asp Lys Phe Leu Gly Arg Trp Phe Ser Ala Gly Leu Ala Ser Asn Ser
            20                  25                  30

Ser Trp Leu Arg Glu Lys Lys Ala Ala Leu Ser Met Ala Lys Ser Val
        35                  40                  45

Val Ala Pro Ala Thr Asp Gly Gly Leu Asn Leu Thr Ser Thr Phe Leu
    50                  55                  60

Arg Lys Asn Gln Cys Glu Thr Arg Thr Trp Leu Leu Gln Pro Ala Gly
65                  70                  75                  80

Ser Leu Gly Ser Tyr Ser Tyr Arg Ser Pro His Trp Gly Ser Thr Tyr
                85                  90                  95

Ser Val Ser Val Val Glu Thr Asp Tyr Asp Gln Tyr Ala Leu Leu Tyr
            100                 105                 110

Ser Gln Gly Ser Lys Gly Pro Gly Glu Asp Phe Arg Met Ala Thr Leu
        115                 120                 125

Tyr Ser Arg Thr Gln Thr Pro Arg Ala Glu Leu Lys Glu Lys Phe Thr
    130                 135                 140

Ala Phe Ala Lys Ala Gln Gly Phe Thr Glu Asp Thr Ile Val Phe Leu
145                 150                 155                 160

Pro Gln Thr Asp Lys Cys Met Thr Glu Gln
                165                 170


<210> SEQ ID NO 10
<211> LENGTH: 66
<212> TYPE: DNA
<213> ORGANISM: Artificial Sequence
<220> FEATURE:
<223> OTHER INFORMATION: Avitag sence primer

<400> SEQUENCE: 10
```

-continued

```
gttccgcgtg gatccatgtc tggcctgaac gatattttcg aagcgcagaa aattgaatgg      60

cacgaa                                                                  66


<210> SEQ ID NO 11
<211> LENGTH: 66
<212> TYPE: DNA
<213> ORGANISM: Artificial Sequence
<220> FEATURE:
<223> OTHER INFORMATION: Avitag antisence primer

<400> SEQUENCE: 11

ctcgggtgcg gatccttcgt gccattcaat tttctgcgct tcgaaaatat cgttcaggcc      60

agacat                                                                  66


<210> SEQ ID NO 12
<211> LENGTH: 174
<212> TYPE: PRT
<213> ORGANISM: Artificial Sequence
<220> FEATURE:
<223> OTHER INFORMATION: Signed Barrier Mutant

<400> SEQUENCE: 12

Gly Ser Ala Pro Glu Ala Gln Val Ser Val Gln Pro Asn Phe Gln Gln
1               5                   10                  15

Asp Lys Phe Leu Gly Arg Trp Phe Ser Ala Gly Leu Ala Ser Asn Ser
            20                  25                  30

Ser Trp Leu Arg Glu Lys Lys Ala Ala Leu Ser Met Ala Lys Ser Val
        35                  40                  45

Val Ala Pro Ala Thr Asp Gly Gly Leu Asn Leu Thr Ser Thr Phe Leu
    50                  55                  60

Arg Lys Asn Gln Cys Glu Thr Arg Thr Trp Leu Leu Gln Pro Ala Gly
65                  70                  75                  80

Ser Leu Gly Ser Tyr Ser Tyr Arg Ser Pro His Trp Gly Ser Thr Tyr
                85                  90                  95

Ser Val Ser Val Val Glu Thr Asp Tyr Asp Gln Tyr Ala Leu Leu Tyr
            100                 105                 110

Ser Gln Gly Ser Lys Gly Pro Gly Glu Asp Phe Arg Met Ala Thr Leu
        115                 120                 125

Tyr Ser Arg Thr Gln Thr Pro Arg Ala Glu Leu Lys Glu Lys Phe Thr
    130                 135                 140

Ala Phe Ala Lys Ala Gln Gly Phe Thr Glu Asp Thr Ile Val Phe Leu
145                 150                 155                 160

Pro Gln Thr Asp Lys Cys Arg Gly Asp Lys Gly Pro Asp Cys
                165                 170
```